(12) United States Patent
Bab et al.

(10) Patent No.: US 6,479,460 B1
(45) Date of Patent: Nov. 12, 2002

(54) SYNTHETIC PEPTIDES AND PSEUDOPEPTIDES HAVING OSTEOGENIC ACTIVITY AND PHARMACEUTICAL COMPOSITIONS CONTAINING THE SAME

(75) Inventors: Itai Bab, Carmei Yossef (IL); Dan Gazit, Jerusalem (IL); Chen Yu-Chen, Jerusalem (IL); Andras Muhlrad, Jerusalem (IL); Arie Shteyer, Mevasserei Zion (IL); Michael Chorev, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/150,621

(22) Filed: Sep. 10, 1998

Related U.S. Application Data

(63) Continuation of application No. PCT/IL97/00087, filed on Mar. 10, 1997.

(30) Foreign Application Priority Data

Mar. 10, 1996 (IL) ................................................. 117426

(51) Int. Cl.$^7$ ........................... A61K 38/08; C07K 7/02
(52) U.S. Cl. ........................... 514/17; 514/18; 530/323; 530/330
(58) Field of Search ................................ 530/330, 323; 514/17, 18

(56) References Cited

U.S. PATENT DOCUMENTS 5,461,034 A    10/1995    Rodan et al. .................. 514/14

FOREIGN PATENT DOCUMENTS

| EP | A-0 384 731 | 8/1990 |
| EP | 572 122 A2 | 12/1993 |
| WO | WO94/20529 | * 9/1994 |

OTHER PUBLICATIONS

Hocart et al. Effect of CH2NH and CH2NAC Peptide Bond Isosteres on the Antagonistic and Histamine Releasing Activities of a Luteinizing Hormone Releasing Hormone Analogue Journal fo Medicinal Chemistry. vol. 31, pp. 1820–1824. (1988).*

Moroder, L. et al., Hoppe Seylers Z. Physiol. Chem. 357(11): 1651–3 (Nov. 1976).

Rickard, D. J. et al., Dev. Biol. 161(1):218–28 (Jan. 1994).

Bab I., et al. Removal of tibial marrow induces increased formation of bone and cartilage in rat mandubular condyle (1985) Calcif. Tissue Int. 37:551–555.

Foldes, J., et al. Osteogenic response to marrow aspiration: increased serum osteocalcin and alkaline phosphatase in human bone marrow donors (1989) J. Bone Min. Res. 4:643–647.

Einhorn, T.A., et al. The Osteogenic response to distant skeletal injury (1990) J. Bone Joint Surg. Am. 72:1374–1378.

Gazit D., et al. Regenerating marrow induces systemic increase in oseto– and chondrogenesis (1990) Endocrinology 126:2607–2613.

Mueller, M., et al. A systemic acceleratory phenomenon (SAP) accompanies the regional acceleratory phenomenon (rap) during healing of a bone defect in the rat (1991) J. Bone Min. Res. 6:401–410.

Bab, I., et al. Histone H4–related osteogenic growth peptide (OGP): a novel circulating stimulator of osteoblastic activity (1992) EMBO J. 11:1867–1873.

Greenberg, Z., et al. Structural and functional characterization of osteogenic Growth peptide from human serum: identity with rat and mouse homologs (1995) J. Clin. Endocrinol. Metab 80:2330–2335.

Morodor, L., et al (1976) Physiol. Chem. 357:1651.

Merrifield (1969) Adv. Enzymol. 32:221.

Stewart, J.M., Young, J.D., (1984) In: Solid Phase Peptide Synthesis. Pierce Chemical Co.: Rockford, IL, pp. 1–75.

Greenberg, Z., et al. Mitogenic action of osteogenic growth peptide (OGP): Role of amino and carboxy–terminal regions and charge (1993) Biochim Biophys Acta 1178:273–280.

Lender, A., et al Design and synthesis of sulfur–free cyclic hexapeptides which contain the rgd sequence and bind to the fibrinogen GP IIb/IIIa receptor (1993) Int. J. Peptide Protein Res., 42:509–517.

Nishino, N., et al Sequence dependence in solid–phase–synthesis cyclization cleavage for cyclo(–arginyl–glycyl–aspartyl–phenylglycyl–) (1992) Tetrahedron Letters, 33:1479–1482.

Cheung, S.T. and Benoiton, N.L., N–Methylamino acids in peptide synthesis V. The synthesis of N–tert–butyloxycarbonyl, N–methylamino acids by N–methylation (1997) Can. J. Chem., 55:906–.

Sasaki, Y. and Coy, D.H., Solid phase synthesis of peptides containing the CH$_2$NH peptide bond isostere (1987) Peptides, 8:119–121.

(List continued on next page.)

*Primary Examiner*—Christopher S. F. Low
*Assistant Examiner*—Anish Gupta
(74) *Attorney, Agent, or Firm*—Robert Kinberg; Keith Haddaway; Venable

(57) ABSTRACT

The invention relates to synthetic pseudopeptide derivatives of osteogenic grog polypeptide (OGP) and OGP(10–14) which may be linear or cyclic, and which are capable of enhancing bone cell proliferation and bone formation. Further, the present invention relates to pharmaceutical composition comprising as active ingredient at least one pseudopeptide derivative of the invention and to the use of these pseudopeptide derivatives in the preparation of a pharmaceutical composition for stimulating the formation of osteoblastic or fibroblastic cells, enhancing bone formation in osteopenic pathological conditions, repairing fractures, healing wounds, grafting of intraosseous implants, reversing bone loss in osteoporosis and other conditions requiring enhanced bone cells formation.

7 Claims, 8 Drawing Sheets

OTHER PUBLICATIONS

Fehrentz, J.–A. and Castro B., An efficient synthesis of optically active α–(t–Butoxycarbonylamino)–aldehydes from α–amino acids (1983) Synthesis, pp. 676–678.

Hocart, S.J., et al Effect of the $CH_2NH$ and $CH_2NAc$ peptide bond isosteres on the antagonistic and histamine relating activities of a lutenizing hormone releasing hormone analogue (1988) J. Med. Chem. 31:1820–1824.

Wilchek, M. and Bayer, E.A., (1990) Methods Enzymol 184:5.

Rickard, D.J., et al (1994) Biology, 161:218.

Bab, I and Einhorn T.M. Polypeptide factors regulating osteogenesis and bone marrow repair (1994) J. Cellular Biochemistry 55:358–365.

Robinson I. et al. Osteogenic growth peptide regulates proliferation and osteogenic maturation of human and rabbit bone marrow stromal cells (1995) J. of Bone and Min. Res. 10(5):690–696.

Bab, I. et al. Regulatory role of osteogenic growth peptide in proliferation, osteogenesis and hemopoiesis (1995) Clinical Orthopaedics and Related Research 313:64–68.

Gurevitch O. et al. Osteogenic growth peptide increases blood and bone marrow cellularity and enhances engraftment of bone marrow transplants in mice (1996) Blood 88(12):4719–4724.

Bab I. Postablation bone marrow regeneration: an in vivo model to study differential regulation of bone formation and resorption (1995) Bone 17(4):437S–441S.

Bab I. Regulatory role of osteogenic growth polypeptide in bone formation and hemopoiesis (1993) Critical Reviews in Eukaryotic Gene Expression 3(1):31–46.

\* cited by examiner

SYNTHETIC PEPTIDES AND PSEUDOPEPTIDES HAVING OSTEOGENIC ACTIVITY AND PHARMACEUTICAL COMPOSITIONS CONTAINING THE SAME

REFERENCES TO RELATED APPLICATION

This application is a continuation of International Application No. PCT/IL97/00087 filed Mar. 10, 1997, and claims priority of Israel Application Ser. No. 117426, filed Mar. 10, 1996, both applications being incorporated herein b4y reference.

BACKGROUND OF THE INVENTION

It has been established that regenerating bone marrow induces an osteogenic response in distant skeletal sites and that this activity is mediated by factors released into the circulation by the healing tissue [(Bab I., et al. (1985) Calcif. Tissue Int. 37:551; Foldes, J., et al. (1989) J. Bone Min. Res. 4:643; Einhorn, T. A., et al. (1990) J. Bone Joint Surg. Am. 72:1374; Gazit D., et al. (1990) Endocrinology 126:2607; Mueller, M., et al. (1991) J. Bone Min. Res. 6:401]. One of these factors, a 14-amino acid osteogenic growth polypeptide (OGP) (SEQ ID NO: 1), identical with the C-terminus of histone H4, has been recently identified in the regenerating bone marrow [Bab, I., et al. (1992) EMBO J. 11:1867; EP-A-0 384 731] and in human serum [Greenberg, Z et al (1995) J. Clin. Endocrinol. Metab 80:2330].

Synthetic osteogenic growth polypeptide, identical in structure with the native molecule, has been shown to be a potent stimulator of proliferation of osteoblastic and fibroblastic cells in vitro. This synthetic polypeptide also stimulates osteoblastic cell alkaline phosphatase activity. When injected in vivo to rats, at very small doses, the synthetic osteogenic growth polypeptide increases bone formation and trabecular bone mass [Bab, I., et al (1992) EMBO J. 11:1867].

Since the OGP molecule is too large for effective oral administration, it is of therapeutic importance to identify peptides, shorter than the full length OGP, that retain the OGP activity and can be modified into a stable preparation, suitable for the oral treatment of several pathological conditions, particularly conditions involving loss of bone tissue. Indeed, it was shown that the C-terminal pentapeptide of OGP, Try-Gly-Phe-Gly-Gly[OGP(10–14)] (SEQ ID NO: 61), retains the full OGP-like proliferative activity in vitro and osteogenic effect in vivo [WO94/20529 corresponding to Israel Patent Application No. 104954]. Due to its small size, this penta-peptide provides a useful basis for the design of further OGP analogs with improved activity, stability and bioavailability.

In search for yet improved osteogenically active substances, the inventors have now found novel, synthetic pseudopeptide derivatives of OGP (SEQ ID NO: 1) and OGP(10–14) (SEQ ID NO: 61), which are the subject of the present application.

BRIEF DESCRIPTION OF THE INVENTION

The present invention relates to pseudopeptidic osteogenic growth polypeptide (OGP) analogs having the general formula:

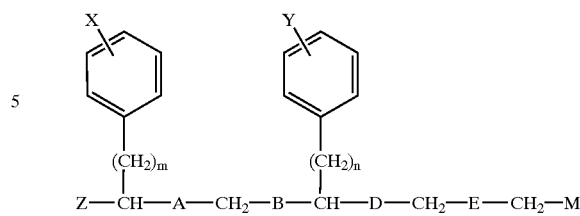

wherein the substituents are as hereafter defined.

The invention also relates to cyclic peptidic or pseudopeptidic OGP analogs having the general formula:

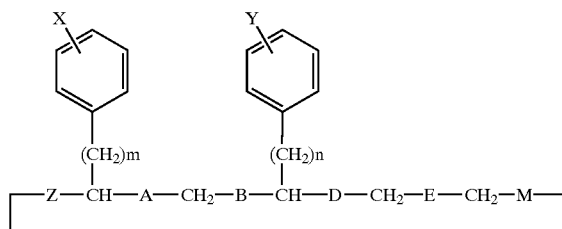

wherein the substituents are as hereafter defined.

The invention also relates to pharmaceutical compositions comprising as active ingredients the compounds of formulae (I) and/or (II).

DETAILED DESCRIPTION OF THE INVENTION

Osteogenic growth polypeptide (OGP) is a 14-residue polypeptide identified from regenerating bone marrow which has been shown to stimulate the proliferation and alkaline phosphatase activity of osteoblastic and fibroblastic cells in vitro and to increase bone formation and trabecular bone mass in rats when injected in vivo. In addition, shorter, tetra—and pentapeptides, derived from the C-terminal of OGP have been identified, which retain the OGP activity. Naturally, such short peptides may have advantages as therapeutic agents, being smaller molecules than the native or synthetic full length OGP. The present invention is concerned with various modifications of these peptides, which may be of major interest as potent agonists and antagonists of OGP.

The present invention thus relates to pseudopeptidic osteogenic growth polypeptide (OGP) analogs having the general formula:

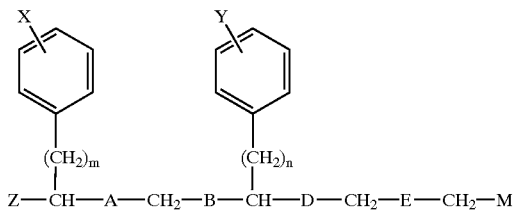

wherein
A, B, D and E, which may be the same or different, represent CONH, $CH_2NH$, $CH_2S$, $CH_2O$, NHCO, $N(CH_3)CO$, $(CH_2)_2$, CH=CH, $C(O)CH_2$, $CH_2SO$ or $C(O)O$, M represents C(O)OH, $CH_2OH$, $C(O)NH_2$, $C(O)OCH_3$, $CH_2OCH_3$, H, $C(O)NHCH_3$, or $C(O)N(CH_3)_2$, Z represents $NH_2$, H, $NHCH_3$, $N(CH_3)_2$, OH, SH, $OCH_3$, $SCH_3$, C(O)OH, $C(O)NH_2$, $C(O)OCH_3$, $C(O)NHCH_3$ or $C(O)N(CH3)_2$, n and m each represent an integer of 1 to 6, X and Y, if in the ortho or para positions, each represent OH, $OCH_3$, F, Cl, Br, $CF_3$, CN, $NO_2$, $NH_2$, $NHCH_3$, $N(CH_3)_2$, SH, $SCH_3$, $CH_2OH$, $NHC(O)CH_3$, C(O)OH, $C(O)OCH_3$, $C(O)NH_2$, $C(O)NHCH_3$, $C(O)N(CH_3)_2$, or $CH_3$, and Y, if in the para or meta positions, represents $C(O)C_6H_5$, $C(O)CH_3$, $C_6H_5$, $CH_2C_6H_5$, and, if in the ortho or para positions can additionally represent $C(O)C_6H_5$, $C(O)CH_3$, $C_6H_5$, $CH_2C_6H_5$, $CH_2CH_3$, $CH(CH_3)_2$, or $C_6H_{11}$ with the proviso that said compounds is not (Tyr-Gly-Phe-Gly-Gly) (SEQ ID NO: 61).

The invention also relates to cyclic peptidic or pseudopeptidic OGP analogs having the general formula:

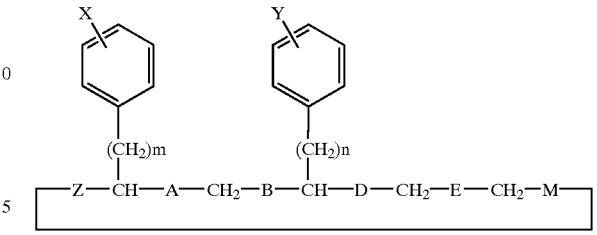

wherein Z—M represent NHC(O), C(O)NH, $CH_2NH$, $NH_2CH_2$, $N(CH_3)C(O)$, $C(O)N(CH_3)$, C(O)O, OC(O), OR $(CH_2)_1$ where 1 is an integer of from 2 to 6 and A, B, D, E, n, m, X and Y are as hereinbefore defined.

Figure 5:
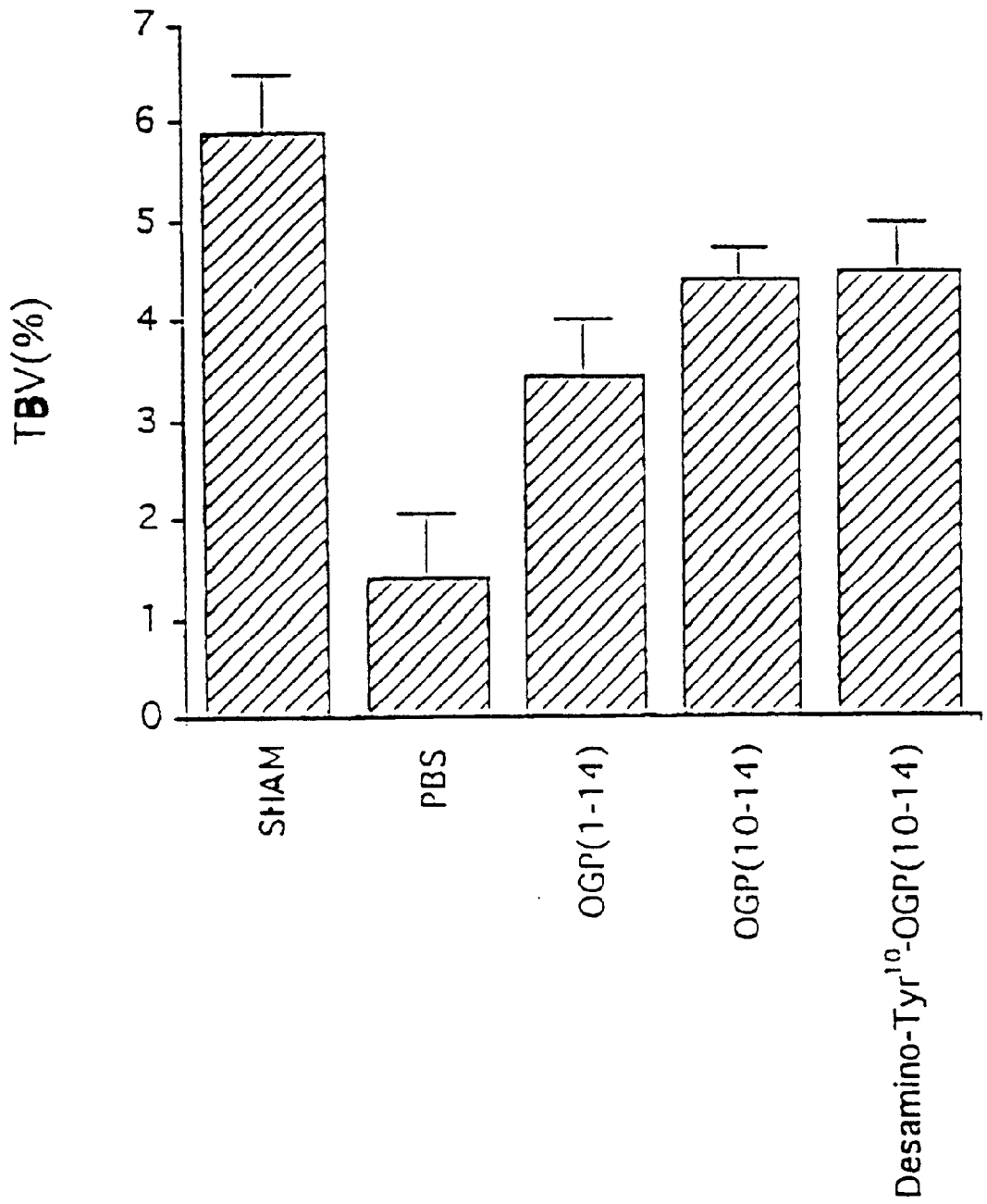
FIG. 5 shows the effect of synthetic OGP analogs on reversal of trabecular bone loss in proximal tibial metaphysis of ovariectomized mice. Data are mean±SE obtained in eight mice per group.

A particular pseudopeptidic OGP analog of formula (I) is desamino Tyr-Gly-Phe-Gly-Gly (SEQ ID NO: 4) (referred to in the following Examples as desamino[Tyr$^{10}$]OGP (10–14)), demonstrating a retention of approximately 70% OGP-like activity (Table 1, analog 4), indicating the minor role of the a-amino group in the OGP activity. Furthermore, in vivo effects of this analog (FIGS. 5,6) were either similar or superior to the parent oligopeptides, namely, OGP(1–14) (SEQ ID NO: 1) and OGP(10–14) (SEQ ID NO: 61).

Other particular pseudopeptidic OGP analogs of formula (I) are desamino Tyr-Gly-N($CH_3$)-CH($CH_2C_6H_5$)-C(O)-Gly-Gly (SEQ ID NO: 32) (referred to in the following Examples as desamino[Tyr$^{10}$,N(Me)-Phe$^{12}$]OGP(10–14)), desamino Tyr-$CH_2$-Gly-Phe-Gly-Gly (SEQ ID NO: 47) (referred to in the following Examples as desamino[Tyr$^{10}$ψ($CH_2NH$)-Gly$^{11}$]OGP(10–14)), desamino Tyr-NH-$CH_2$-$CH_2$-Phe-Gly-Gly (SEQ ID NO: 48) (referred to in the following Examples as desamino[Tyr$^{10}$,Gly$^{11}$ψ($CH_2NH$)Phe$^{12}$]OGP(10–14)), desamino Tyr-Gly-NH-CH ($CH_2C_6H_5$)-$CH_2$-Gly-Gly (SEQ ID NO: 49) (referred to in the following Examples as desamino[Tyr$^{10}$,Phe$^{12}$ψ($CH_2NH$)Gly$^{13}$]OGP(10–14)), desamino Tyr-Gly-Phe-NH-$CH_2$-$CH_2$-Gly (SEQ ID NO: 50) (referred to in the following Examples as to desamino[Tyr$^{10}$,Gly$^{13}$ψ($CH_2NH$)Gly$^{14}$] OGP(10–14)), desamino Tyr-Gly-Phe-NH-$CH_2$-$CH_2$-$CH_2$-C(O)-OH (SEQ ID NO: 51) (referred to in the following Examples as desamino[Tyr$^{10}$,Gly$^{13}$ψ($CH_2$)$_2$ Gly$^{14}$]OGP(10–14)), Tyr-Gly-NH-CH($CH_2C_6H_4$(C(O)-$C_6H_5$))C(O)-Gly-Gly (SEQ ID NO: 56) (referred to in the following Examples as [Bpa$^{12}$]OGP(10–14)), Tyr(m-I)-Gly-NH-CH($CH_2C_6H_4$(C(O)$C_6H_5$))C(O)-Gly-Gly (SEQ ID NO: 57) (referred to in the following Examples as [Tyr$^{10}$(m-I), Bpa$^{12}$]OGP(10–14)) and Nα-biotinylcaproyl[Bpa$^{12}$]OGP (10–14) (SEQ ID NO: 58), all showing in vitro potency, relative to that of OGP, of above 0.5, similar or improved activity compared to desamino[Tyr$^{10}$]OGP(10–14) (SEQ ID NO: 4) (Tables 5,6).

A particular cyclic peptidic OGP analog of formula (II) is:

(SEQ ID NO: 35)

Tyr-Gly-Phe-Gly-Gly [00023]

Figure 2:
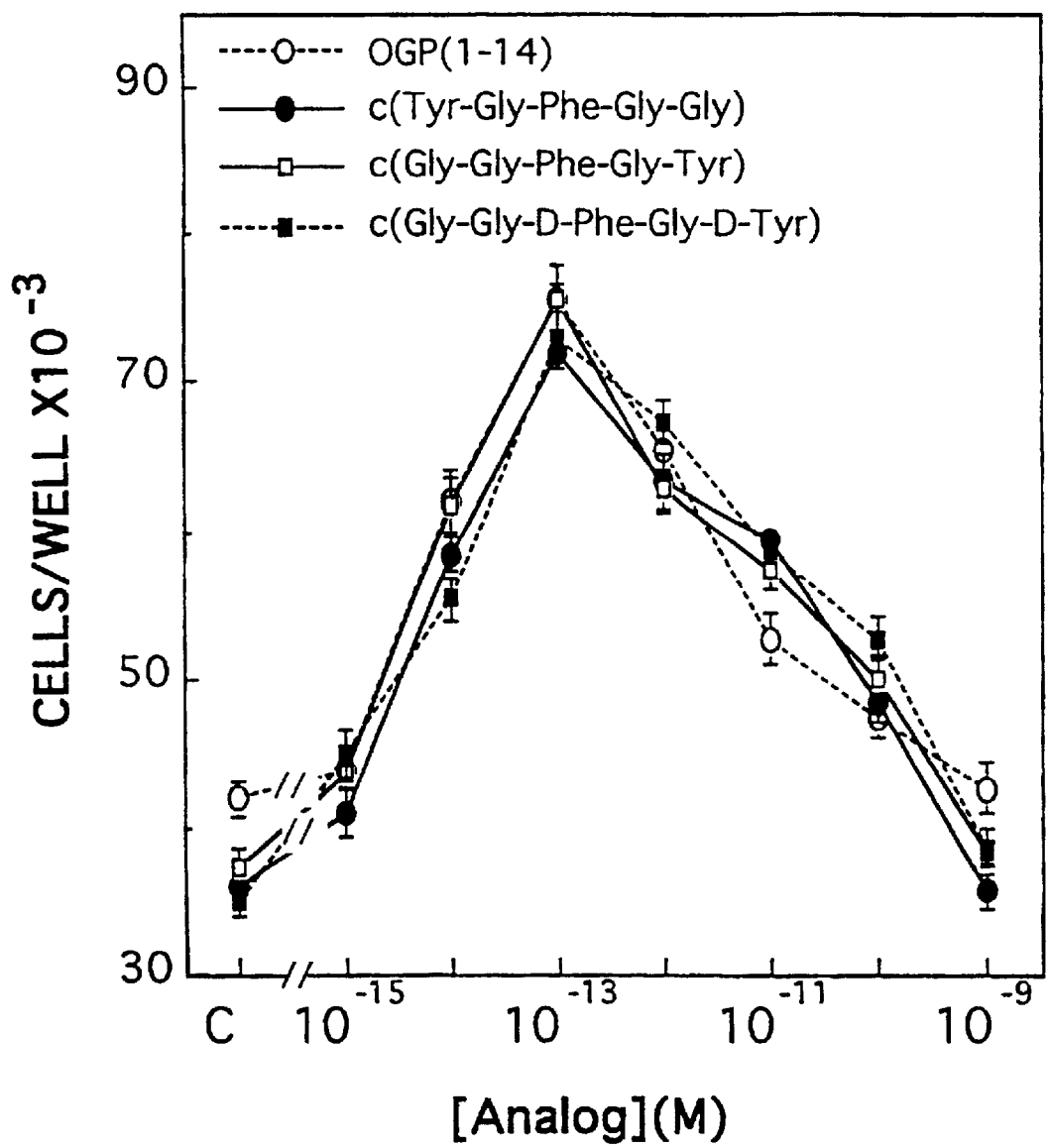
FIG. 2 shows the dose-response relationship of proliferative activity of cyclic OGP analogs in cultures of osteoblastic MC3T3E1 cells as compared with negative control cultures not treated with any peptide (C) and positive control cultures treated with synthetic OGP(1–14) (SEQ ID NO: 1). Data are mean±SE obtained in three culture wells per condition.

(referred to in the following Examples as c[Tyr-Gly-Phe-Gly-Gly]. This cyclization is another mode to rigidify the OGP(10–14) structure. As can be seen in FIG. 2 this rigidification preserves the OGP-like in vitro activity. In addition, FIG. 6 exhibits an improved in vivo activity of c[Tyr-Gly-Phe-Gly-Gly] (SEQ ID NO: 35) over OGP (10–14). Also, introduction of D-amino acids into this cyclic peptide, as, for

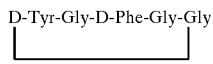
D-Tyr-Gly-D-Phe-Gly-Gly example (referred to in the following Examples as c[D-Tyr-Gly-D-Phe-Gly-Gly]) resulted in a peptide which had a considerable level of proliferative activity.

Other particular cyclic peptidic or pseudopeptidic OGP analogs of formula (II) are:

Gly-Gly-Phe-Gly-Tyr (SEQ ID NO: 37)

(referred to in the following Examples as c[Gly-Gly-Phe-Gly-Tyr]), and

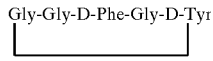
Gly-Gly-D-Phe-Gly-D-Tyr preferred to in the following Examples as c[Gly-Gly-D-Phe-Gly-D-Tyr]) demonstrating a similar or slightly improved in vitro activity (Table 5). Interestingly, the retro analog, in which the sequence of the amino acids was reversed, retained a full OGP-like proliferative activity, suggesting the irrelevance of amide bond direction in the backbone. This observation is also displayed in the constrained, linear pseudopeptides, as shown in Table 5. The improved efficacy of the present constrained analogs might be due to increased resistance to peptidase degradation and longer persistence in circulation or increased potency and bioavailability, as described in the following Examples.

Figure 7:
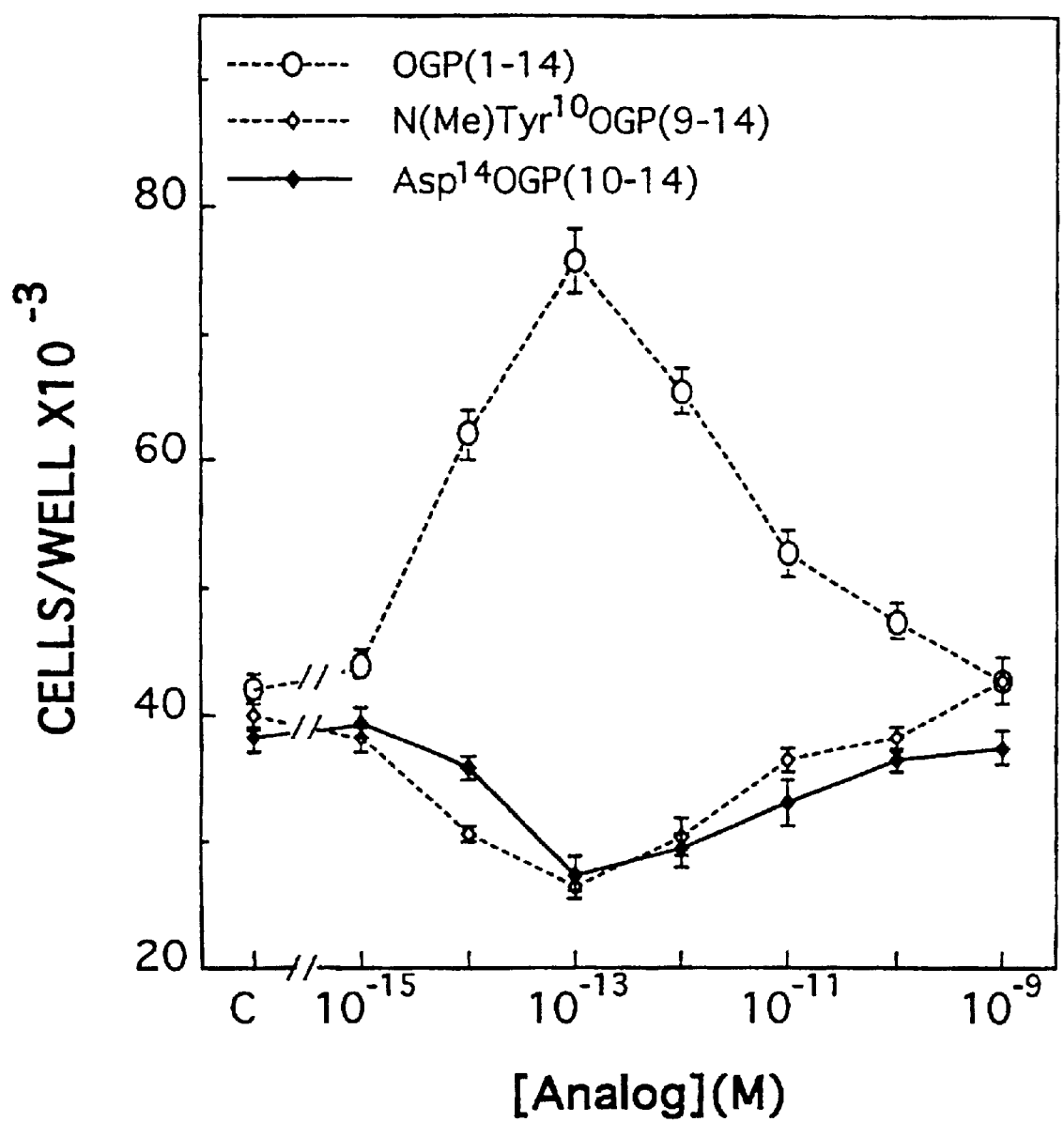
FIG. 7 shows the dose-response inhibition of stimulatory effect of optimal OGP(1–14) (SEQ ID NO: 1) dose on osteoblastic MC3T3E1 cell as compared with negative control cultures not treated with any peptide (C). All other cultures were treated with $10^{-13}$M synthetic OGP(1–14) (SEQ ID NO: 1) and the indicated dose of antagonist. Data are mean±SE obtained in three culture wells per condition.

In addition, the invention relates to peptidic and pseudopeptidic osteogenic growth polypeptide antagonists such as, for example, Leu-N(CH$_3$)-CH(CH$_2$C$_6$H$_4$(OH))-C(O)-Gly-Phe-Gly-Gly (SEQ ID NO: 59) ([N(CH$_3$)-Tyr$^{10}$] OGP(9–14)) as herein defined) and Tyr-Gly-Phe-Gly-Asp (SEQ ID NO: 29) ([Asp$^{14}$]OGP(10–14)). As can be seen in FIG. 7, the present antagonists have an inhibitory effect at low doses on stimulation by an optimal OGP(10–14) dose on osteoblastic MC3T3 E1 cells. Moreover, in the absence of exogenous OGP(10–14) the present antagonists demonstrate an anti-proliferative activity in the MC3T3 E1 cells. Nevertheless, a reversal effect is obtained at higher doses, thus showing a dose-dependent response to [N(CH$_3$)Tyr$^{10}$] OGP(9–14) (SEQ ID NO: 59) and [Asp$^{14}$]OGP(10–14) (SEQ ID NO: 29). These antagonists may be useful in the treatment of conditions characterized by excess OGP.

The invention also relates to pharmaceutical compositions comprising as active ingredient a pseudopeptide of formula (I), optionally with a pharmaceutically acceptable carrier.

Particularly preferred are pharmaceutical compositions in which said pseudopeptide is desamino[Tyr$^{10}$]OGP(10–14) (SEQ ID NO: 4).

A further aspect the invention relates to pharmaceutical compositions comprising as active ingredient a cyclic peptide or pseudopeptide of formula (II), optionally with a pharmaceutically acceptable carrier. Pharmaceutical compositions in which said cyclic peptide is c[Tyr-Gly-Phe-Gly-Gly] (SEQ ID NO: 35) are preferred.

The pseudopeptides of formula (I) and cyclic peptides or pseudopeptides of formula (II) may be particularly useful in the preparation of pharmaceutical compositions for stimulating the formation of osteoblastic or fibroblastic cells, enhancing bone formation in osteopenic pathological conditions, repairing fractures, healing wounds, grafting of intraosseous implants, reversing bone loss in osteoporosis and other conditions requiring enhanced bone cells formation.

EXAMPLES

Materials and Methods

General

Boc-amino acids were purchased from either Bachem, California or prepared with ditert.butyl dicarbonate by conventional procedure [Morodor, L., et al (1976) Physiol. Chem. 357:1651]. All chemicals were purchased from Aldrich Chemical Co., Fluka Chemie AG or Pierce Chemical Co. and were of analytical grade. Peptidic and pseudopeptidic OGP analogs were treated with liquid HF in an all-Teflon apparatus (Protein Research Foundation, Osaka, Japan). Thin layer chromatography (TLC) was performed on precoated silica gel plates 60F-254 (E. Merck, Darmstadt, FRG) in the following solvent systems (all v/v): (i) 1-BuOH/AcOH/H$_2$O (4:1:1); (ii) 1-BuOH/AcOH/EtOAc/H$_2$O (5:1:3:1); (iii) CHCl$_3$/MeOH/AcOH (9:3:1). Analogs were visualized by UV light and/or ninhydrine staining. Analytical and semipreparative HPLC separations were performed on a Merck Hitachi 655A-11 apparatus, equipped with 655A Variable Wavelength and L-5000 LC Controller, D-2000 Chromato-Integrator and an AS-2000 Autosampler injector. Light absorbance was recorded at 220 nm. A reverse phase Lichrospher 100 C-18 column was used for all analytical applications. The crude OGP analogs were purified on a μBondpark C-18, 19×150 mm or a Vydac Protein & Peptide C-18 column employing acetonitrile containing 0.1% (v/v) trifluoroacetic acid in water. Flow rates were 1 ml/min for the analytical column and 6 ml/min for the semipreparative column.

Synthesis of OGP Analogs

Unless otherwise indicated, the peptidic or pseudopeptidic OGP analogs of this invention were prepared manually on a Milligen 504 Synthesizer or automatically using a 401A Applied Biosystem Peptide Synthesizer. Boc-Amino acids were assembled on a PAM resin, Merrifield resin, Oxime resin or MBHA resin [Merrifield (1969) Adv. Enzymol. 32:221]. The fully assembled analog was removed from the resin either by ammonolysis or the HF procedure.

The preparations were evaluated for purity using analytical HPLC (Vydac C-18 column) and were shown to be more than 95% pure. The molecular weight of the analogs was verified by Fast Atom Bombardment Mass Spectroscopy (FAB-MS). When applicable the analogs were subjected to amino acid analysis.

Introduction of C-terminal Modifications

C-terminal modifications were introduced by coupling an active ester with the corresponding amine component either during cleavage from the resin or later in solution [Stewart, J. M., Young, J. D., (1984) In: Solid Phase Peptide Synthesis. Pierce Chemical Co.: Rockford, Ill., pp. 1–75].

Preparation of Cyclic Analogs

N- to C-terminal cyclization was carried out in a low concentration (0.008 M) solution of the corresponding linear peptide in amine-free dimethylformamide (DMF) at 0° C. The coupling agent was diphenol-phosphoryl azide (1.5 equivalent) [Lender, A., et al (1993) Int. J. Peptide Protein Res., 42:509]. Upon completion of the reaction the solvent was removed by evaporation and the cyclic analog purified by reverse phase HPLC.

N-terminal to side chain cyclization was carried out with the peptide chain assembled on an Oxime resin. After the removal of the N-terminal protecting group the Oxime resin-bound peptide was subjected to a cyclization-cleavage step [Nishino, N., et al (1992) Tetrahedron Letters, 33:1479].

Preparation of Analogs With N-methylated Boc-amino Acids

The Boc-amino acid used for preparation of the corresponding analogs was dissolved in dry methyl iodide supplemented tetrahydrofurane. N-methylation was induced by NaH. The solvent was removed in vacuuo and the crude product purified by flash column chromatography eluted with EtOAc-petroleum ether [Cheung, S. T. and Benoiton, N. L., (1977) Can. J. Chem., 55:906].

N-terminal Acetylation

Following N-terminal deprotection and prior to cleavage, the resin bound peptide was treated with acetyl hydride and N,N-diisopropylethylamine (DIEA).

Introduction of Reduced Amide Bonds

The introduction of the $\psi(CH_2NH)$ peptide bond isostere into the corresponding peptides was accomplished by solid phase reaction of the N-terminal amino group of the resin bound peptide with the requisite Boc-protected amino acid aldehyde in the presence of sodium cyanoborohydride in DMF containing 1% AcOH [Sasaki, Y. and Coy, D. H., (1987) Peptides, 8:119]. The corresponding aldehydes were prepared by $LiAlH_4$ reduction [Fehrentz, J.-A. and Castro B., (1983) Synthesis, pp. 676–678] of their N,O-dimethyl hydroxamates [Hocart, S. J., et al (1988) J. Med. Chem. 31:1820].

Preparation of Nα-Biotinylcaproyl-OGP(10–14) (SEQ ID NO: 58)

The purified OGP(10–14) (SEQ ID NO: 61) was dissolved in dry DMF containing an equivalent of DIEA and biotin reagent. The reaction mixture was adjusted to pH 8.5 with DIEA. The crude product was neutralized with AcOH and the solvents removed in vacuuo [Wilchek, M. and Bayer, E. A., (1990) Methods Enzymol 184:5].

Proliferation Assay

The effect of OGP analogs on osteoblastic MC3T3 E1 and fibroblastic NIH 3T3 cell proliferation was measured as before [Bab, I., et al (1992) EMBO J. 11:1867]. Some of the analogs were subjected to a dose response analysis. Otherwise the analog concentration was $10^{-13}M$ and $10^{-11}M$ in the MC3T3 E1 and NIH3T3 cell cultures, respectively. The mean cell number in triplicate culture wells was expressed as percent of a positive control triplicate dosed with OGP (1–14) (SEQ ID NO: 1). Experiments testing one dose per cell line were repeated at least four times and the activity of individual analogs expressed as the mean of results and 95% confidence limit obtained in these repetitive experiments.

Osteogenic Effect of OGP Analogs in Ovariectomized Mice

Thirty two female C57B1/6 mice weighing 25 gm underwent conventional bilateral ovariectomy (OVX). Additional eight control animals were subjected to sham OVX: the anterior abdominal wall was opened and the ovaries exposed but left intact. All animals were left untreated for 30 days. The OVX animals were then divided into four groups each consisting of eight mice. All animals were injected subcutaneously in the nape daily for six weeks with the following solutions: One group was given OGP(1–14) (SEQ ID NO: 1), 30 ng/day/mouse. A second group received OGP(10–14) (SEQ ID NO: 61), 10 ng/day/mouse. A third group was given desamino[Tyr$^{10}$]OGP(10–14) (SEQ ID NO: 4). All compounds were dissolved in phosphate buffered saline (PBS). An additional control OVX group was given the PBS solvent only. One day after termination of treatment the animals were killed and the tibial bones separated, fixed in phosphate buffered formalin and subjected to conventional decalcified histological processing. Sections through the midsagital region of the tibia were stained with Masson trichrome. Bone volume was determined in the secondary spongiosa of the proximal metaphysis in two sections 200–300 μm apart from each other in one tibia from each animal using an automated computerized image analyzer. The value for each animal was the mean reading from the two sections.

Effect of OGP Analogs on the Number of Bone Marrow Derived Osteoblastic Colonies from Ovariectomized Rats Twenty five female Sabra rats weighing 250 g each were subjected to bilateral ovariectomy (OVX). Additional five control animals underwent sham OVX. All animals were left untreated for 30 days. Then the OVX animals were divided into five groups, each consisting of five rats. All animals were injected subcutaneously in the nape daily for eight weeks with following solutions: One group was given to OGP(10–14) (SEQ ID NO: 61), 100 ng/day/rat. A second group was given desamino[Tyr$^{10}$]OGP(10–14) (SEQ ID NO: 4), 100 ng/day/rat. A third group was given c(Tyr-Gly-Phe-Gly-Gly) (SEQ ID NO: 35), 100 ng/day/rat. The fourth group was given retro OGP (Gly-Gly-Phe-Gly-Tyr-Leu-Thr-Arg-Gly-Gln-Arg-Lys-Leu-Ala) (SEQ ID NO: 60), 300 ng/day/rat. All compounds were dissolved in PBS. An additional control OVX group was given the PBS solvent only. After termination of treatment the animals were killed and the femoral and tibial bone marrow from both posterior limbs was pooled and transferred to alpha minimal essential medium (αMEM). Bone marrow cell cultures were set in 35 mm dishes, 10 dishes per animal, as described previously [Rickard, D. J., et al (1994) Biology, 161:218]. The total number of fibroblastic colonies (CFU-f) formed was determined after three weeks in culture. Immediately after, the CFU-f cultures were stained for alkaline phosphates and co-stained for mineral with alizarin-red-S. The alizarin-red-S positive colonies were considered osteoblastic. Their frequency was expressed as their percentage of the total numbers of colonies. The value for each animal was calculated as the mean percentage obtained in the 10 dishes.

Results

Figure 1:
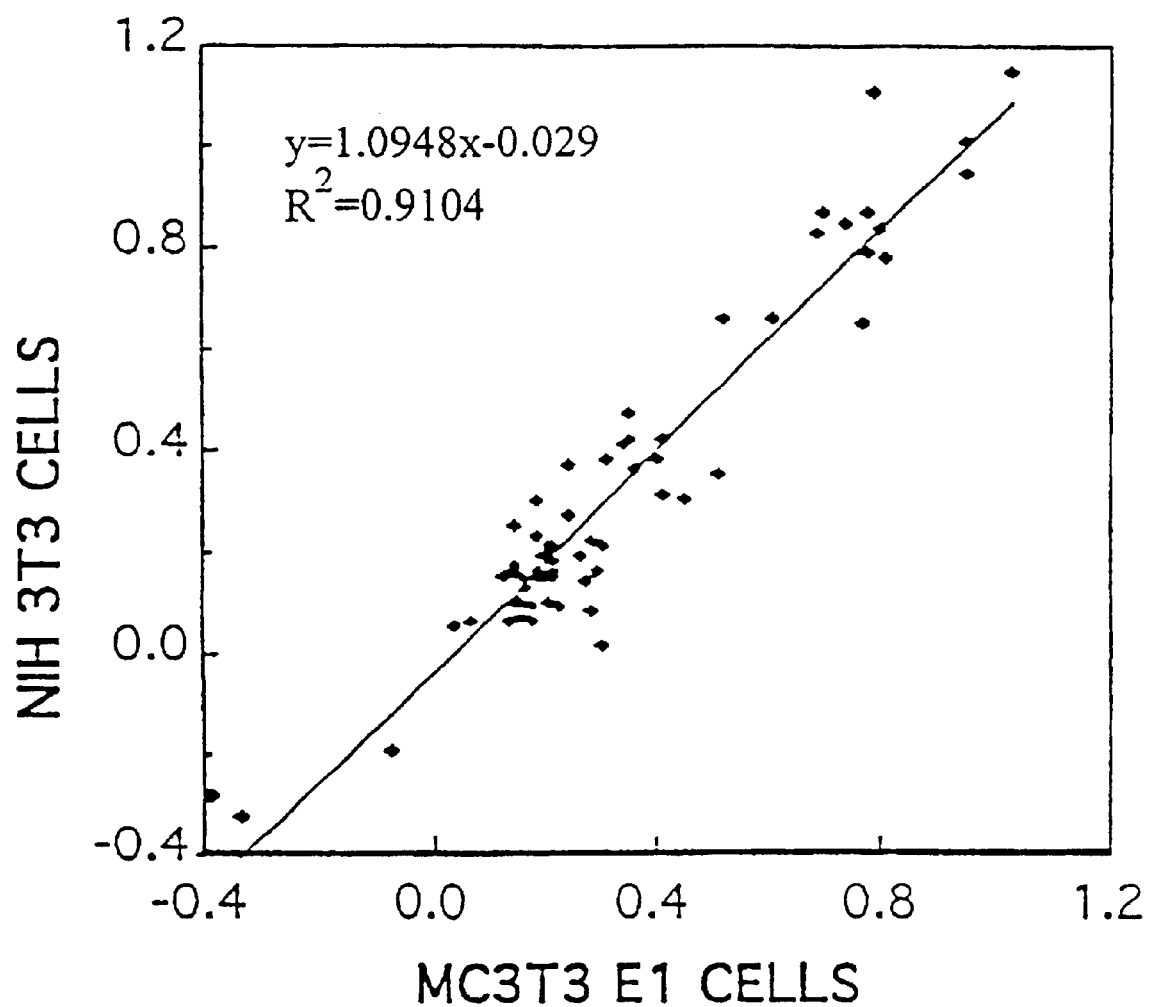
FIG. 1 shows the linear regression of proliferative activity of OGP (SEQ ID NO: 1) between osteoblastic MC3T3E1 and fibroblastic NIH3T3 cells.

The proliferative activity of synthetic OGP analogs is shown in Tables 1–6. There was a very high correlation of the proliferative activity of the analogs between the osteoblastic MC3T3 E1 and fibroblastic NIH3T3 cells (FIG. 1). The scatter plot of the MC3T3 E1/NIH3T3 relationship (FIG. 1) demonstrates three clusters of analogs, namely (i) those with activity higher than 50% compared to OGP(1–14) (SEQ ID NO: 1); (ii) those showing less than 50% activity compared to OGP(1–14) (SEQ ID NO: 1); and (iii) those that inhibit cell proliferation. Only one analog, desamino [Tyr$^{10}$]OGP(10–14)-OMe (SEQ ID NO: 8), could not be assigned to one cluster in the sense that it showed slightly more than 50% activity in the MC3T3 E1 cells and less than 50% activity in the NIH3T3 cells (Table 1, analog 8). The activity of few analogs, [Bpa$^{12}$]OGP(10–14) (SEQ ID NO: 56) (Table 7, analog 2), [Tyr$^{10}$(m-I), Bpa$^{12}$]OGP(10–14) (SEQ ID NO: 57) (Table 7, analog 3), [Pro$^{11}$]OGP(10–14) (SEQ ID NO: 30) (Table 5, analog 2), desamino[Tyr$^{10}\psi$(CH$_2$NH)Gly$^{11}$]OGP(10–14) (SEQ ID NO: 47) (Table 6, analog 2), desamino[Tyr$^{10}$,Gly$^{13}\psi$(CH$_2$NH)Gly$^{14}$]OGP (10–14) (SEQ ID NO: 50) (Table 6, analog 5), desamino [Tyr$^{10}$,Gly$^{13}\psi$(CH$_2$)$_2$Gly$^{14}$]OGP(10–14) (SEQ ID NO: 51) (Table 6, analog 6Gly-Phe-Gly-Gly) (SEQ ID NO: 35) (Table 5, analog 7), c(Gly-Gly-Phe-Gly-Tyr) (SEQ ID NO: 37) (Table 5, analog 9) and c(Gly-Gly-D-Phe-Gly-D-Tyr)

Figure 3A:
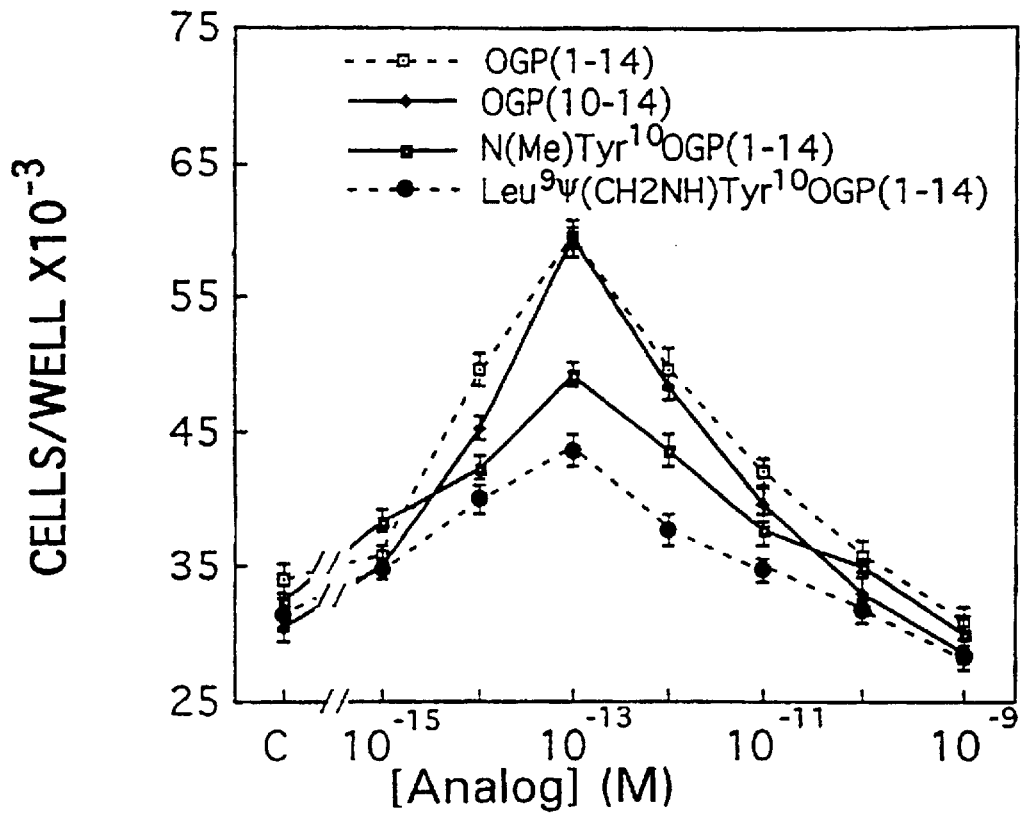
FIGS. 3A and 3B show the dose-response relationship of proliferative activity of constrained OGP analogs with substitution of the peptide bond between Leu$^9$ and Tyr$^{10}$ in cultures of osteoblastic MC3T3E1 (A) and fibroblastic NIH3T3 (B) cells as compared with negative control cultures not treated with any peptide (C) and positive control cultures treated with synthetic OGP(1–14) (SEQ ID NO: 1) or OGP(10–14) (SEQ ID NO: 61). Data are mean±SE obtained in three culture wells per condition.
Figure 3B:
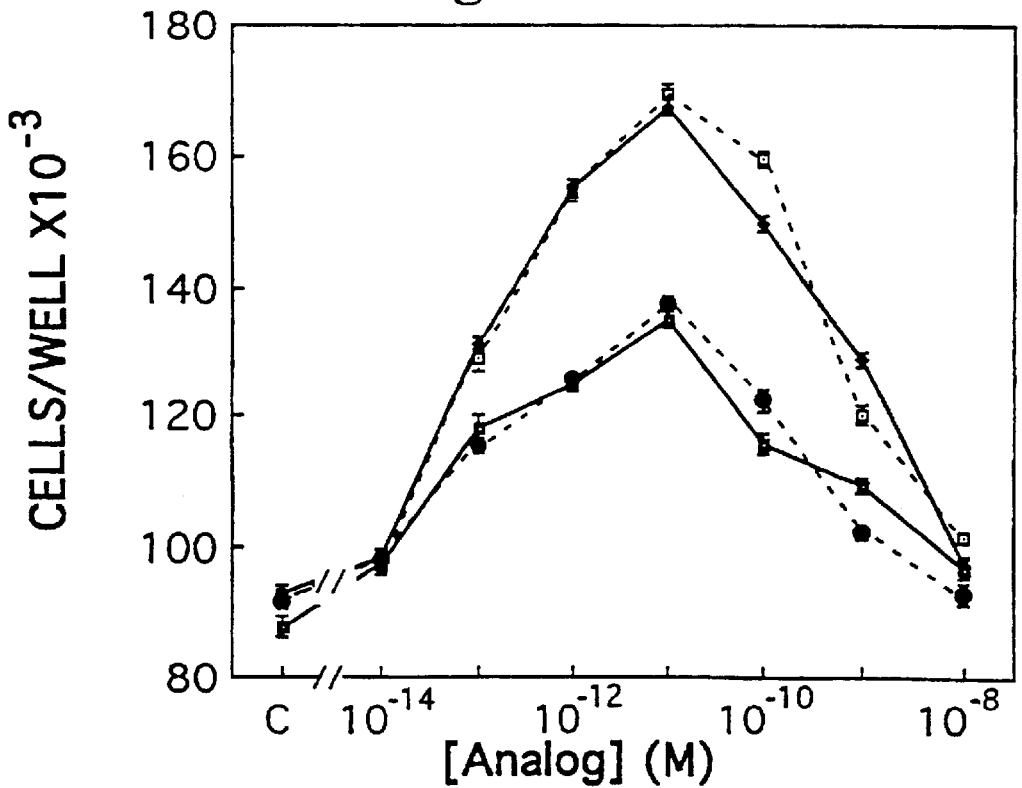
Figure 4A:
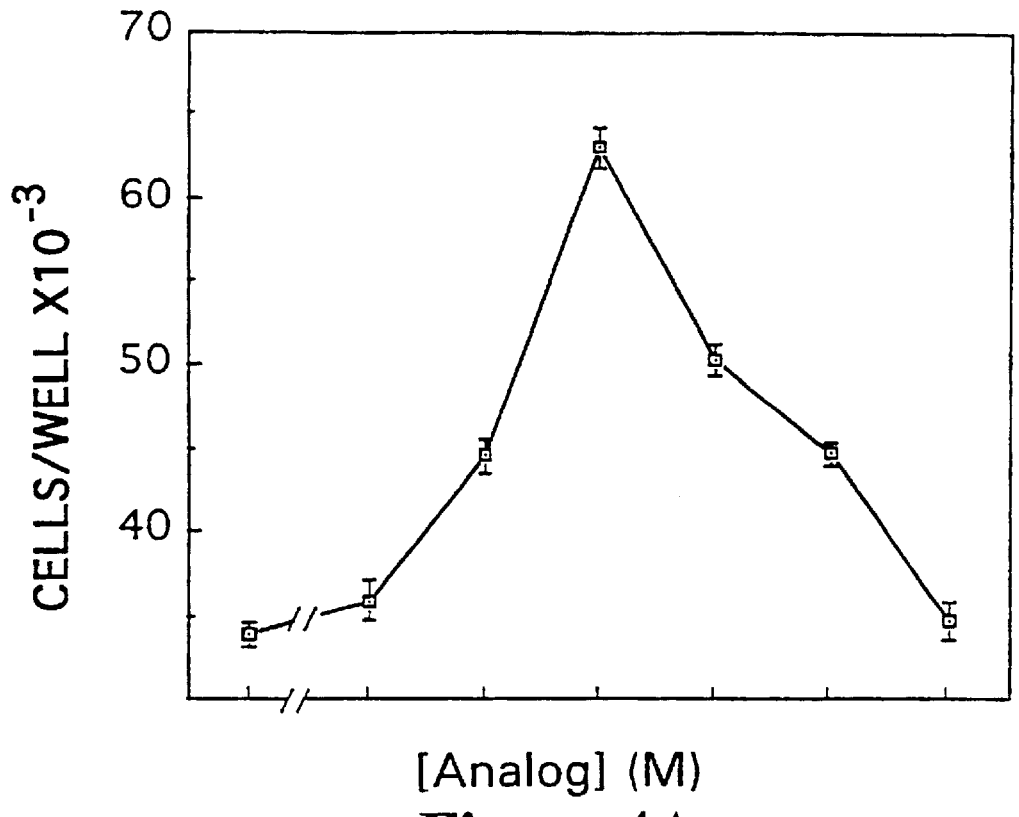
FIGS. 4A and 4B show the dose-response relationship of proliferative activity of photoreactive OGP analogs in cultures of osteoblastic MC3T3E1 cells as compared with negative control cultures not treated with any peptide (C) and positive control cultures treated with synthetic OGP (1–14) (SEQ ID NO: 1) or OGP(10–14) (SEQ ID NO: 61). A-[Bpa$^{12}$]OGP(10–14) (SEQ ID NO: 56); B-±Nα-biotinylcaproyl-[Bpa$^{12}$]OGP(10–14) (SEQ ID NO: 58) and positive controls. Data are mean±SE obtained in three culture wells per condition.
Figure 4B:
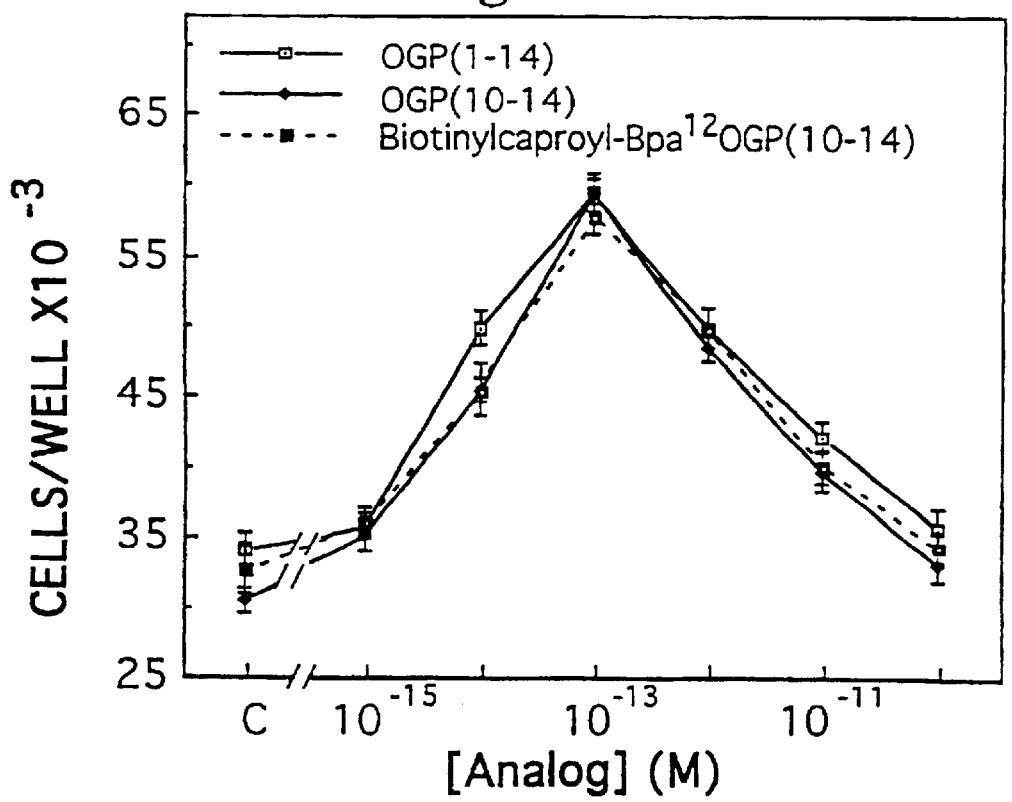

(Table 5, analog 11), was similar to that of OGP(1–14) (SEQ ID NO: 1) or even higher. The activity of Nα-Ac-OGP (12–14) (SEQ ID NO: 3) (Table 1, analog 3), desamino [Tyr$^{10}$]OGP(10–13)NH(CH$_2$)$_2$ OMe (SEQ ID NO: 12) (Table 1, analog 12), [Ala$^{11}$]OGP(11–14) (SEQ ID NO: 14) (Table 2, analog 2), [Gly$^{13}$ψ(CH$_2$)$_2$Gly$^{14}$]OGP(11–14) (SEQ ID NO: 52) (Table 6, analog 7), c(β-Ala-Tyr-Gly-Phe-Gly-Asp)-OH (SEQ ID NO: 44) (Table 5, analog 18) and c(γ-Abu-Tyr-Gly-Phe-Gly-Asp) (SEQ ID NO: 45) (Table 5, analog 19), was essentially nil. Some of the analogs were subjected to a dose-response analysis in the MC3T3E1 and NIH3T3 cell proliferation assays. The resulting biphasic dose-response curve was similar to that of OGP(1–14) (SEQ ID NO: 1) and OGP(10–14) (SEQ ID NO: 61) [Bab, I., et al. (1992) EMBO J. 11:1867; Greenberg, Z., et al (1993) Biochim Biophys Acta 1178:273] with a dose-dependent stimulation at low concentrations followed by a dose-dependent reversal of this stimulation at high doses. The peak response in the MC3T3 E1 and NIH3T3 cells was at $10^{-13}$M and $10^{-11}$M peptide concentration, respectively (FIGS. 2–4).

Amino terminal group analysis indicated that the a-amine group has only a small role in the OGP activity as demonstrated by the retention of approximately 70% OGP-like activity by desamino[Tyr$^{10}$]OGP(10–14) (SEQ ID NO: 4) (Table 1, analog 4). The in vivo effects of this analog, namely, the respective reversal of trabecular bone loss and reduction in osteoprogenitor cells in osteoporotic OVX mice and rats, were either similar or superior to those of OGP (1–14) (SEQ ID NO: 1) and OGP(10–14) (SEQ ID NO: 61) (FIGS. 5,6) probably because of increased resistance to degradation by amino peptidases. Removal of Tyr$^{10}$ (Table 1, analog 2 (SEQ ID NO: 2); Table 2, analog 2(SEQ ID NO: 14)) or its replacement by L-Ala (SEQ ID NO: 17) (Table 2, analog 5), D-Ala (Table 2, analog 5), desaminoAla (SEQ ID NO:19) (Table 2, analog 7), Phe (SEQ ID NO: 24) (Table 3, analog 2), desaminoPhe (SEQ ID NO: 25) (Table 3, analog 3) or (desaminoPhe)$_2$ (SEQ ID NO:26) (Table 3, analog 4) resulted in loss of more than 70% activity.

TABLE 1

Proliferative activity of OGP(10–14) analogs with modified termini

| Analog | Relative in vitro potency (95% confidence limit) | |
|---|---|---|
| | MC3T3 E1 cells | NIH 3T3 cells |
| 1 OGP(1–4) (SEQ ID NO: 1) | 1.00 (standard) | 1.00 (standard) |
| 2 Nα-Ac—OGP(11–14) (SEQ ID NO: 2) | 0.21 (0.17–0.25) | 0.22 (0.17–0.27) |
| 3 Nα-Ac—OGP(12–14) (SEQ ID NO: 3) | 0.06 (0.02–0.11) | 0.07 (0.03–0.11) |
| 4 desamino[Tyr$^{10}$]OGP(10–14) (SEQ ID NO: 4) | 0.77 (0.66–0.88) | 0.66 (0.54–0.78) |
| 5 OGP(11–14)-ol (SEQ ID NO: 5) | 0.24 (0.20–0.29) | 0.38 (0.35–0.42) |

TABLE 1-continued

Proliferative activity of OGP(10–14) analogs with modified termini

| Analog | Relative in vitro potency (95% confidence limit) | |
|---|---|---|
| | MC3T3 E1 cells | NIH 3T3 cells |
| 6 desamino[Tyr$^{10}$]OGP(10–14)—NH$_2$ (SEQ ID NO: 6) | 0.20 (0.05–0.35) | 0.16 (0.05–0.27) |
| 7 desamino[Tyr$^{10}$]OGP(10–14)—ol (SEQ ID NO: 7) | 0.24 (0.14–0.34) | 0.28 (0.14–0.42) |
| 8 desamino[Tyr$^{10}$]OGP(10–14)—OMe (SEQ ID NO: 8) | 0.51 (0.43–0.59) | 0.36 (0.29–0.43) |
| 9 desamino[Tyr$^{10}$]OGP(10–14)—NHMe (SEQ ID NO: 9) | 0.18 (0.06–0.30) | 0.16 (0.08–0.28) |
| 10 desamino[Tyr$^{10}$]OGP(10–14)—N(Me)$_2$ (SEQ ID NO: 10) | 0.12 (0.08–0.21) | 0.16 (0.05–0.27) |
| 11 desamino[Tyr$^{10}$]OGP(10–13)—NH(CH$_2$)$_2$NH$_2$ (SEQ ID NO: 11) | 0.18 (0.07–0.29) | 0.17 (0.06–0.28) |
| 12 desamino[Tyr$^{10}$]OGP(10–13)—NH(CH$_2$)$_2$OMe (SEQ ID NO: 12) | 0.03 (0.00–0.06) | 0.06 (0.01–0.11) |
| 13 desamino[Tyr$^{10}$]OGP(10–13)—NHEt (SEQ ID NO: 13) | 0.19 (0.02–0.36) | 0.20 (0.11–0.31) |

Because of its high in vitro and particularly in vivo OGP-like activity, the desamino[Tyr$^{10}$]OGP(10–14) (SEQ ID NO: 4) was used as a basis for carboxy terminal modifications and L-and D-Ala scanning. This analysis shows that at least in a linear structure the intact Gly$^4$ is essential significant level of mitogenic activity inasmuch as all analogs with carboxy terminal group modifications, except maybe desamino[Tyr$^{10}$]OGP(10–14)-OMe (SEQ ID NO: 8), lost most the OGP-like activity (Table 1).

The replacement of individual amino acids in both OGP (10–14) (SEQ ID NO: 61) and desamino Tyr$^{10}$(10–14) (SEQ ID NO: 4) by L- or D-Ala or even desamination of Gly$^{11}$ resulted in all cases in substantial loss of OGP-like proliferative activity (Tables 2, 4). These findings further suggest that in both the MC3T3E1 and NIH3T3 cell systems (i) the aromatic ring of Phe$^{12}$ is essential for a significant level of OGP-like proliferative activity; (ii) the spatial relationship between the phenolic OH group of Tyr$^{10}$ and aromatic ring of Phe$^{12}$, including the distance between these groups, may be also important for this activity. In disagreement with the Ala substitution of Gly$^3$ is the replacement of this residue by His which has no consequences upon the activity of OGP (10–14) (SEQ ID NO: 61) [WO94/20529 corresponding to Israel Patent Application No. 104954]. Substitution of Gly$^{14}$ by Asp resulted in a highly potent OGP antagonist (Table 3, FIG. 7).

TABLE 2

Proliferative activity of OGP(10–14) analogs with L- or D-Ala substitutions

| | Analog | Relative in vitro potency (95% confidence limit) | |
|---|---|---|---|
| | | MC3T3 E1 cells | NIH 3T3 cells |
| 1 | OGP(1–4) (SEQ ID NO: 1) | 1.00 (standard) | 1.00 (standard) |
| 2 | [Ala$^{11}$]OGP(11–14) (SEQ ID NO: 14) | 0.17 (0.12–0.23) | 0.07 (0.03–0.12) |
| 3 | [Ala$^{13}$]OGP(11–14) (SEQ ID NO: 15) | 0.22 (0.14–0.29) | 0.10 (0.05–0.15) |
| 4 | [Ala$^{14}$]OGP(11–14) (SEQ ID NO: 16) | 0.17 (0.12–0.23) | 0.10 (0.06–0.13) |
| 5 | [Ala$^{10}$]OGP(10–14) (SEQ ID NO: 17) | 0.29 (0.19–0.39) | 0.17 (0.04–0.30) |
| 6 | [Ala$^{11}$]OGP(10–14) (SEQ ID NO: 18) | 0.18 (0.13–0.22) | 0.31 (0.24–0.37) |
| 7 | desamino[Ala$^{10}$]OGP(10–14) (SEQ ID NO: 19) | 0.28 (0.07–0.49) | 0.09 (0.00–0.18) |
| 8 | desamino[Tyr$^{10}$,Ala$^{12}$]OGP(10–14) (SEQ ID NO: 20) | 0.41 (0.29–0.53) | 0.43 (0.38–0.48) |
| 9 | desamino[Tyr$^{10}$,Ala$^{12}$]OGP(10–14) (SEQ ID NO: 21) | 0.21 (0.12–0.30) | 0.16 (0.06–0.26) |
| 10 | desamino[Tyr$^{10}$,Ala$^{13}$]OGP(10–14) (SEQ ID NO: 22) | 0.27 (0.23–0.31) | 0.15 (0.09–0.21) |
| 11 | desamino[Tyr$^{10}$,Ala$^{14}$]OGP(10–14) (SEQ ID NO: 23) | 0.19 (0.04–0.34) | 0.16 (0.06–0.26) |
| 12 | [D-Ala$^{10}$]OGP(10–14) | 0.12 (0.00–0.25) | 0.16 (0.05–0.27) |
| 13 | [D-Ala$^{13}$]OGP(10–14) | 0.14 (0.13–0.16) | 0.26 (0.20–0.31) |
| 14 | desamino[Tyr$^{10}$,D-Ala$^{11}$]OGP(10–14) | 0.21 (0.00–0.55) | 0.19 (0.09–0.29) |
| 15 | desamino[Tyr$^{10}$,D-Ala$^{12}$]OGP(10–14) | 0.30 (0.13–0.47) | 0.02 (0.00–0.06) |
| 16 | desamino[Tyr$^{10}$,D-Ala$^{13}$]OGP(10–14) | 0.28 (0.19–0.37) | 0.23 (0.12–0.34) |
| 17 | desamino[Tyr$^{10}$,D-Ala$^{14}$]OGP(10–14) | 0.41 (0.27–0.55) | 0.32 (0.17–0.47) |

TABLE 3

Proliferative activity of OGP(10–14) analogs with Phe substitution of Tyr$^{10}$

| | Analog | Relative in vitro potency (95% confidence limit) | |
|---|---|---|---|
| | | MC3T3 E1 cells | NIH 3T3 cells |
| 1 | OGP(1–14) (SEQ ID NO: 1) | 1.00 (standard) | 1.00 (standard) |
| 2 | [Phe$^{10}$]OGP(10–14) (SEQ ID NO: 24) | 0.41 (0.27–0.55) | 0.32 (0.17–0.47) |
| 3 | desamino[Phe$^{10}$]OGP(10–14) (SEQ ID NO: 25) | 0.35 (0.28–0.42) | 0.48 (0.42–0.54) |
| 4 | (desamino[Phe$^{10}$]$_2$OGP(10–14) (SEQ ID NO: 26) | 0.18 (0.15–0.22) | 0.24 (0.14–0.33) |

TABLE 4

Proliferative activity of OGP(10–14) analogs with modifications at position 11 and 14

| | Analog | Relative in vitro potency (95% confidence limit) | |
|---|---|---|---|
| | | MC3T3 E1 cells | NIH 3T3 cells |
| 1 | OGP(1–4) (SEQ ID NO: 1) | 1.00 (standard) | 1.00 (standard) |
| 2 | des[Gly$^{11}$]OGP(10–14) (SEQ ID NO: 27) | 0.21 (0.17–0.25) | 0.17 (0.11–0.23) |
| 3 | [β-Ala$^{11}$]OGP(10–14) (SEQ ID NO: 28) | 0.29 (0.24–0.34) | 0.17 (0.13–0.21) |
| 4 | [Asp$^{14}$]OGP(10–14) (SEQ ID NO: 29 | −0.39 (−0.26—0.52) | −0.28 (−0.14—0.42) |

Figure 6:
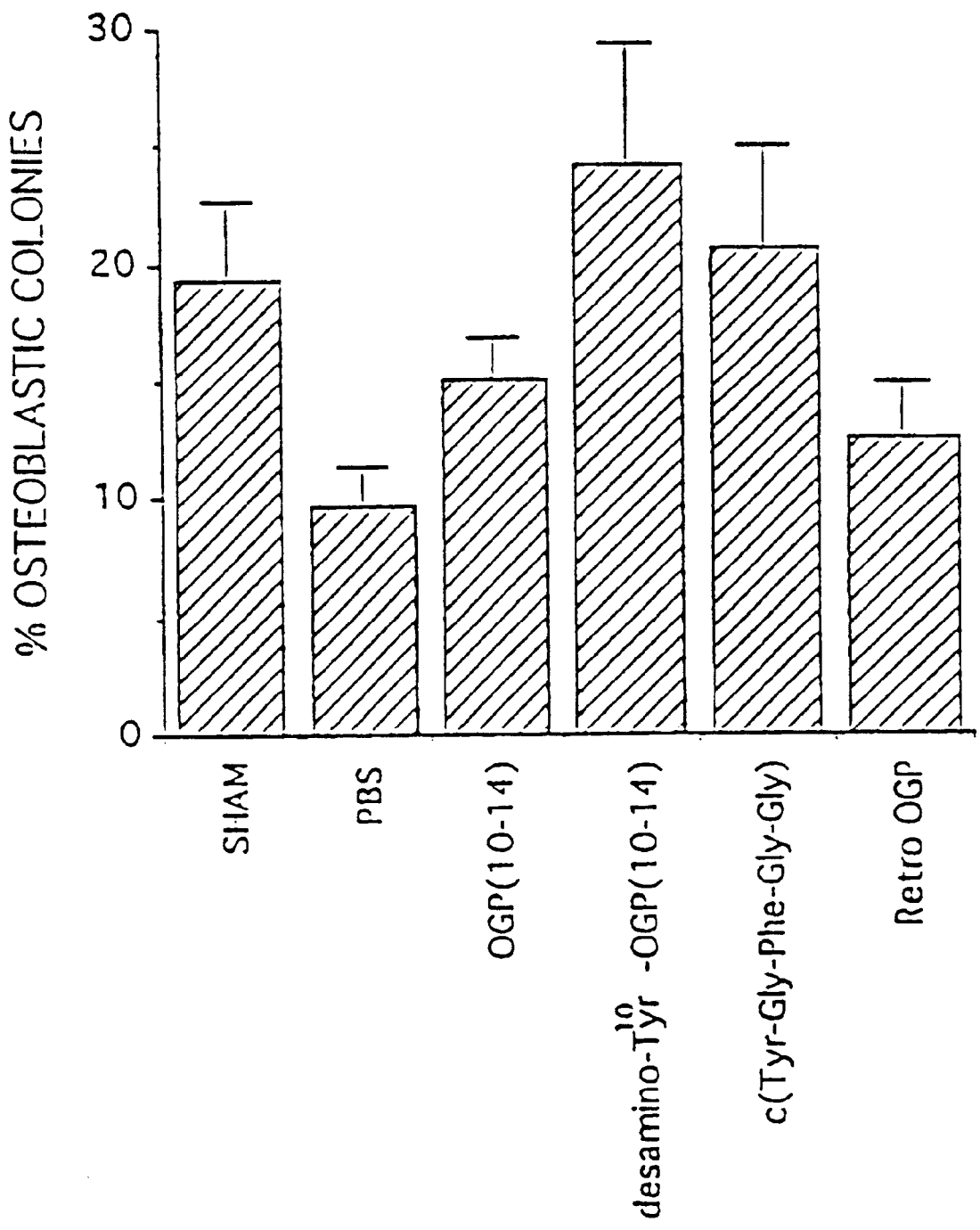
FIG. 6 shows the effect of OGP analogs on reversal of reduction in osteoprogenitor cells in bone marrow of ovariectomized rats as reflected in number of bone marrow derived in vitro osteoblastic colonies. Data are mean±SE obtained in five rats per group.

Most of the structurally constrained OGP analogs show similar or improved activity as compared to the full length OGP (SEQ ID NO: 1). The activity remained essentially unaltered following replacement of Gly$^{11}$ by Pro (SEQ ID NO: 30) (Table 5, analog 2). Rigidification of the OGP (10–14) structure by cyclization also preserved or slightly improved its in vitro activity as demonstrated by the analogs c(Tyr-Gly-Phe-Gly-Gly) (SEQ ID NO: 35) (Table 5, analog 7), c(Gly-Gly-Phe-Gly-Tyr) (SEQ ID NO: 37) (Table 5, analog 9) and c(Gly-Gly-D-Phe-Gly-D-Tyr) (Table 5, analog 11) (FIG. 2). c(D-Tyr-Gly-D-Phe-Gly-Gly) (Table 5, analog 10) also retained a considerable level of proliferative activity. In addition, the in vivo activity of c(Tyr-Gly-Phe-Gly-Gly) (SEQ ID NO: 35) (Table 5, analog 7), i.e. reversal of the OVX induced reduction in bone marrow derived osteoprogenitor cells and osteoblastic colonies, was improved over OGP(10–14) (SEQ ID NO: 61) (FIG. 6). The introduction of constraints which may alter the Tyr/Phe relationship resulted in less active, or in many instances almost inactive, OGP analogs. Structurally constrained peptide-based drugs usually present improved efficacy as a consequence of their increased (i) resistance to peptidase degradation and longer persistence in the circulation; (ii) potency and thus improved cellular responsiveness; (iii) bioavailability through non-parenteral routes, e.g. oral.

TABLE 5

Proliferative activity of constrained OGP analogs

| | Analog | Relative in vitro potency (95% confidence limit) MC3T3 E1 cells | Relative in vitro potency (95% confidence limit) NIH 3T3 cells |
|---|---|---|---|
| 1 | OGP(1–4) (SEQ ID NO: 1) | 1.00 (standard) | 1.00 (standard) |
| 2 | [Pro$^{11}$]OGP(10–14) (SEQ ID NO: 30) | 0.89 (0.80–0.98) | 0.96 (0.87–1.05) |
| 3 | desamino[Tyr$^{10}$,Sar$^{11}$]OGP(10–14) (SEQ ID NO: 31) | 0.31 (0.25–0.37) | 0.39 (0.26–0.52) |
| 4 | desamino[Tyr$^{10}$,N(Me)-Phe$^{12}$]OGP(10–14) (SEQ ID NO: 32) | 0.52 (0.46–0.58) | 0.67 (0.55–0.70) |
| 5 | desamino[Tyr$^{10}$,Sar$^{13}$]OGP(10–14) (SEQ ID NO: 33) | 0.15 (0.07–0.23) | 0.11 (0.05–0.70) |
| 6 | desamino[Tyr$^{10}$,Sar$^{11}$]OGP(10–14) (SEQ ID NO: 34) | 0.16 (0.10–0.22) | 0.14 (0.09–0.19) |
| 7 | c(Tyr-Gly-Phe-Gly-Gly) (SEQ ID NO: 35) | 0.79 (0.72–0.86) | 1.12 (1.06–1.17) |
| 8 | c(Tyr-Cly-Phe-Gly) (SEQ ID NO: 36) | 0.35 (0.30–0.40) | 0.43 (0.40–0.46) |
| 9 | c(Gly-Gly-Phe-Gly-Tyr) (SEQ ID NO: 37) | 0.95 (0.89–1.01) | 1.02 (...0.93–1.11) |
| 10 | c(D-Tyr-Gly-D-Phe-Gly-Gly) | 0.69 (.62–0.76) | 0.84 (0.80–0.88) |
| 11 | c(Gly-Gly-D-Phe-Gly-D-Tyr) | 1.03 (0.95–1.11) | 1.16 (1.10–1.22) |
| 12 | c(Gly-Tyr-Gly-Phe-Gly-Gly) (SEQ ID NO: 38) | 0.26 (0.19–0.33) | 0.20 (0.17–0.23) |
| 13 | c(β-Ala-Tyr-Gly-Phe-Gly-Gly) (SEQ ID NO: 39) | 0.36 (0.30–0.42) | 0.37 (0.31–0.43) |
| 14 | c(γ-Abu-Tyr-Gly-Phe-Gly-Gly) (SEQ ID NO: 40) | 0.20 (0.16–0.24) | 0.22 (0.19–0.25) |
| 15 | c(δ-Ala-Tyr-Gly-Phe-Gly-Gly) (SEQ ID NO: 41) | 0.14 (0.09–0.19) | 0.18 (0.13–0.23) |
| 16 | c(Tyr-Gly-Phe-Gly-Asp)-OH (SEQ ID NO: 42) | 0.14 (0.09–0.19) | 0.11 (0.07–0.15) |
| 17 | c(Gly-Tyr-Gly-Phe-Gly-Asp)-OH (SEQ ID NO: 43) | 0.15 (0.11–0.19) | 0.16 (0.12–0.20) |
| 18 | c(β-Ma-Tyr-Gly-Phe-Gly-Asp)-OH (SEQ ID NO: 44) | −0.08 (−0.04– −0.12) | −0.19 (−0.15– −0.23) |
| 19 | c(γ-Abu-Tyr-Gly-Phe-Gly-Asp)-OH (SEQ ID NO: 45) | 0.13 (0.10–0.16) | 0.07 (0.03–0.11) |
| 20 | c(δ-Ala-Tyr-Gly-Phe-Gly-Asp)-OH (SEQ ID NO: 46) | 0.20 (0.14–0.26) | 0.11 (0.09–0.13) |

The following pseudopeptide analogs of OGP(10–14): desamino[Tyr$^{10}$ψ(CH$_2$NH)Gly$^{11}$]OGP(10–14) (SEQ ID NO: 47) (Table 6, analog 2), desamino[Tyr$^{10}$,Gly$^{11}$ψ(CH$_2$NH)Phe$^{12}$]OGP(10–14) (SEQ ID NO: 48) (Table 6, analog 3), desamino[Tyr$^{10}$,Phe$^{12}$ψ(CH$_2$NH)Gly$^{13}$]OGP (10–14) (SEQ ID NO: 49) (Table 6, analog 4), desamino[Tyr$^{10}$,Gly$^{13}$ψ(CH$_2$NH)Gly$^{14}$]OGP(10–14) (SEQ ID NO: 50) (Table 6, analog 5) desamino[Tyr$^{10}$,Gly$^{13}$ψ(CH$_2$)$_2$Gly$^{14}$]OGP(10–14) (SEQ ID NO: 51) (Table 6, analog 6), had a similar or improved activity compared to desamino[Tyr$^{10}$]OGP(10–14) (SEQ ID NO: 4) (Table 1, analog 4) also because of increased resistance to peptidase degradation.

TABLE 6

Proliferative activity of non-constrained pseudopeptide OGP analogs

| | Analog | Relative in vitro potency (95% confidence limit) MC3T3 E1 cells | Relative in vitro potency (95% confidence limit) NIH 3T3 cells |
|---|---|---|---|
| 1 | OGP(1–14) (SEQ ID NO: 1) | 1.00 (standard) | 1.00 (standard) |
| 2 | desamino[Tyr$^{10}$ψ(CH$_2$NH)Gly$^{11}$]OGP(10–14) (SEQ ID NO: 47) | 0.81 (0.71–0.91) | 0.79 (0.67–0.91) |
| 3 | desamino[Tyr$^{10}$,Gly$^{11}$ψ(CH$_2$NH)Phe$^{12}$]OGP(10–14) (SEQ ID NO: 48) | 0.61 (0.53–0.69) | 0.67 (0.60–0.74) |
| 4 | desamino[Tyr$^{10}$,Phe$^{12}$ψ(CH$_2$NH)Gly$^{13}$]OGP(10–14) (SEQ ID NO: 49) | 0.70 (0.65–0.75) | 0.88 (0.76–1.00) |
| 5 | desamino[Tyr$^{10}$,Gly$^{13}$ψ(CH$_2$NH)Gly$^{14}$]OGP(10–14) (SEQ ID NO: 50) | 0.78 (0.73–0.83) | 0.80 (0.67–0.93) |
| 6 | desamino[Tyr$^{10}$Gly$^{13}$ψ(CH$_2$)$_2$Gly$^{14}$]OGP(10–14) (SEQ ID NO: 51) | 0.78 (0.73–0.83) | 0.188 (0.79–0.97) |
| 7 | [Gly$^{13}$ψ(CH$_2$)$_2$Gly$^{14}$]OGP(11–14) (SEQ ID NO: 52) | 0.15 (0.11–0.19) | 0.08 (0.05–0.13) |
| 8 | N(Me)-[Tyr$^{10}$]OGP(9–14) (SEQ ID NO: 53) | −0.34 (−0.19—0.49) | −0.32 (−0.27—−0.37) |

TABLE 6-continued

Proliferative activity of non-constrained pseudopeptide OGP analogs

| Analog | Relative in vitro potency (95% confidence limit) | |
|---|---|---|
| | MC3T3 E1 cells | NIH 3T3 cells |
| 9  N(Me)-[Tyr$^{10}$]OGP(1–14) | 0.34 | 0.42 |
|    (SEQ D NO: 54) | (0.27–0.41) | (0.35–0.49) |
| 10 [Leu$^9$ψ(CH$_2$NH)Tyr$^{10}$]OGP(1–14) | 0.45 | 0.31 |
|    (SEQ ID NO: 55) | (0.41–0.49) | (0.29–0.33) |

Figure 8:
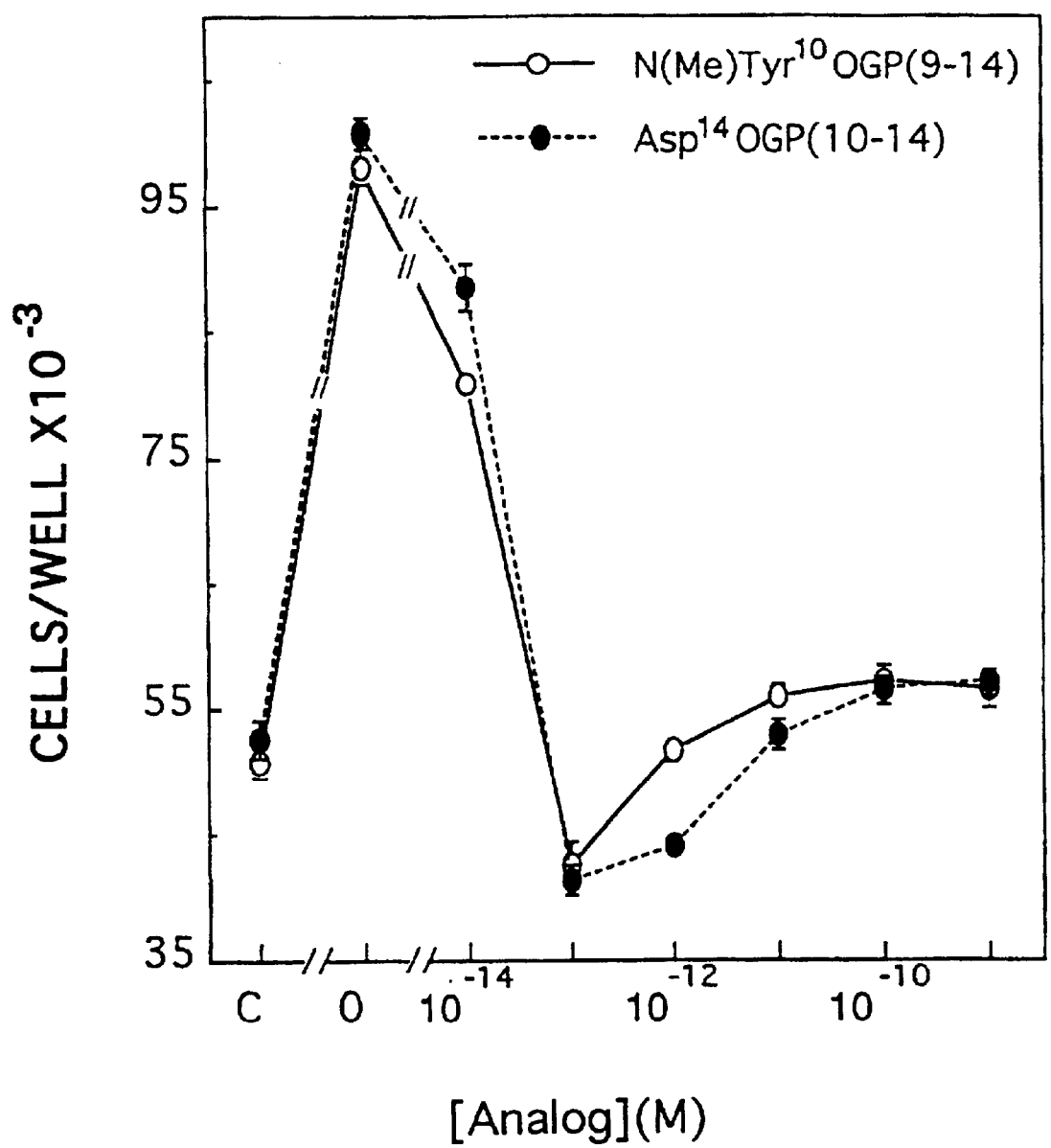
FIG. 8 shows the dose-response relationship of anti-proliferative activity of OGP antagonists in cultures of osteoblastic MC3T3E1 cells as compared with negative control cultures not treated with any peptide (C) and positive control cultures treated with synthetic OGP(1–14) (SEQ ID NO: 1). Data are mean±SE obtained in three culture wells per condition.

Since OGP(10–14) (SEQ ID NO: 61) is a naturally occurring peptide [WO94/20529 responding to Israel Patent Application No. 104954] the dependence of the OGP(1–14) (SEQ NO: 1) mitogenic activity on OGP(10–14) (SEQ ID NO: 61) formation by proteolysis was assessed using the analogs [N(Me)-Tyr$^{10}$]OGP(1–14) (SEQ ID NO: 54) (Table 6, analog 9) and [Leu$^9$ψ(CH$_2$NH)Tyr$^{10}$]OGP(1–14) (SEQ ID NO: 55) (Table 6, analog 10). Either substitution of the natural peptide bond between Leu$^9$ and Tyr$^{10}$ resulted in more than 50% inhibition of the OGP(1–14) activity (Table 6, FIG. 3), suggesting that OGP(10–14) (SEQ ID NO: 61) is essential for the full OGP-like activity. However, truncation of the eight N-terminal amino acid residues of one of these analogs yielded another highly potent OGP antagonist, [N(Me)-Tyr$^{10}$]OGP(9–14) (SEQ ID NO: 53) (Table 6, analog 8) (FIG. 7). In the absence of exogenous OGP both antagonists, [N(Me)-Tyr$^{10}$]OGP(9–14) (SEQ ID NO: 53) and [Asp$^{14}$]OGP(10–14) (SEQ ID NO: 29), inhibit osteoblastic MC3T3 E1 cell proliferation dose dependently at low concentrations with reversal of this inhibition at high doses. The analog concentration evoking the peak inhibitory response is $10^{-13}$ M (FIG. 8). The peak stimulatory response to OGP is seen at the same peptide dose [Bab, I., et al. (1992) EMBO J. 11:1867; Greenberg, Z., et al (1993) Biochim Biophys Acta 1178:273; Greenberg, Z., et al (1995) J. Clin. Endocrinol. Metab 80:2330; U.S. Pat. No. 5,461,034]. This dose-response pattern suggests that [N(Me)-Tyr$^{10}$]OGP (9–14) (SEQ ID NO: 53) and [Asp$^{14}$]OGP(10–14) (SEQ ID NO: 29) antagonize not only the effect of exogenously administered OGP but also the regulatory action of endogenous OGP [Bab, I., et al. (1992) EMBO J. 11:1867; Greenberg, Z., et al (1995) J. Clin. Endocrinol. Metab 80: 2330] and may therefore be used to neutralize undesirable OGP-like responses particularly in instances characterized by excess endogenous OGP.

A benzoyl was introduced in position 4 of the Phe$^{12}$ aromatic ring (SEQ ID NO:56) (Table 7, analog 2) to assess the feasibility of photoaffinity crosslinking of an OGP probe to the putative OGP receptor. This modification had only a minor effect on the OGP-like proliferative activity (FIG. 4). This activity remained unaltered following iodination of Tyr$^{10}$ or addition of a biotinylcaproyl group to the N-terminal of [Bpa$^{12}$]OGP(10–14) (SEQ ID NO: 56) (Table 7, FIG. 4, suggesting that either analog, [Tyr$^{10}$(m-I),Bpa$^{12}$] OGP(10–14) (SEQ ID NO: 57) or Nα-biotinylcaproy)-[Bpa$^{12}$]OGP(10–14) (SEQ ID NO: 58), is a useful tagged, photoreactive ligand.

TABLE 7

Proliferative activity of labeled and/or photoreactive OGP(10–14) analogs

| Analog | Relative in vitro potency (95% confidence limit) | |
|---|---|---|
| | MC3T3 E1 cells | NIH 3T3 cells |
| 1  OGP(1–14) | 1.00 | 1.00 |
|    (SEQ ID NO: 1) | (standard) | (standard) |
| 2  [Bpa$^{12}$]OGP(10–14)* | 0.74 | 0.86 |
|    (SEQ ID NO: 56) | (0.66–0.83) | (0.75–0.97) |
| 3  [Tyr$^{10}$(m-I),BPA$^{12}$]OGP(10–14) | 0.80 | 0.85 |
|    (SEQ ID NO: 57) | (0.74–0.86) | (0.76–0.94) |
| 4  Nα-biotinylcaproyl-[BPA$^{12}$]OGP(10–14)** | | |
|    (SEQ ID NO: 58) | | |

*See FIG. 4 for dose response curve.
**Tested once in triplicate culture wells - see FIG. 4 for dose response curve.

What is claimed is:

1. Pseudopeptidic osteogenic growth polypeptide (OGP) analogs having the general formula

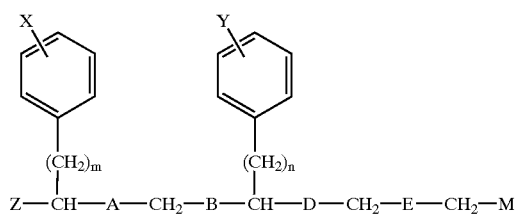

wherein

A, B, D and E, which may be the same or different, represent CONH, $CH_2NH$, $CH_2S$, $CH_2O$, NHCO, $N(CH_3)CO$, $(CH_2)_2$, CH=CH, $C(O)CH_2$, $CH_2SO$ or C(O)O, M represents C(O)OH, $CH_2OH$, $C(O)NH_2$, $C(O)OCH_3$, $CH_2OCH_3$, H, $C(O)NHCH_3$, or $C(O)N(CH_3)_2$, Z represents $NH_2$, H, $NHCH_3$, $N(CH_3)_2$, OH, SH, $OCH_3$, $SCH_3$, C(O)OH, $C(O)NH_2$, $C(O)OCH_3$, $C(O)NHCH_3$ or $C(O)N(CH_3)_2$, n and m each represent an integer of from 1 to 6, X and Y, if in the ortho or para positions, each represent OH, $OCH_3$, F, Cl, Br, $CF_3$, CN, $NO_2$, $NH_2$, $NHCH_3$, $N(CH_3)_2$, SH, $SCH_3$, $CH_2OH$, $NHC(O)CH_3$, C(O)OH, $C(O)OCH_3$, $C(O)NH_2$, $C(O)NHCH_3$, $C(O)N(CH_3)_2$, or $CH_3$, and Y, if in the meta position, represents $C(O)C_6H_5$, $C(O)CH_3$, $C_6H_5$, and, if in the ortho or para positions can additionally represent $C(O)C_6H_5$, $C(O)CH_3$, $C_6H_5$, $CH_2 C_6H_5$, $CH_2CH_3$, $CH(CH_3)_2$, or $C_6H_{11}$ with the proviso that said compound is not Tyr-Gly-Phe-Gly-Gy (SEQ ID NO 61).

2. A pseudopeptidic OGP analog selected from: desamino Tyr-Gly-Phe-Gly-Gly (SEQ ID NO: 4) (desamino[$Tyr^{10}$] OGP(10–14)), desamino Tyr-Gly-N($CH_3$)-CH($CH_2C_6H_5$)-C (O)-Gly-Gly (SEQ ID NO: 32) (desamino[$Tyr^{10}$,N(Me)-$Phe^{12}$]OGP(10–14)), desamino[CH($CH_2C_6H_5OH$)]Tyr-$CH_2$Gly-Phe-Gly-Gly (SEQ ID NO: 47) (desamino[$Tyr^{10}\psi$($CH_2NH$)$Gly^{11}$]OGP(10–14)), desamino Tyr-NH-$CH_2$-$CH_2$-Phe-Gly-Gly (SEQ ID NO: 48) (desamino[$Tyr^{10}$, $Gly^{11}\psi(CH_2NH)Phe^{12}$]OGP(10–14)), desamino Tyr-Gly-NH-CH($CH_2C_6H_5$)-$CH_2$-Gly-Gly (SEQ ID NO: 49) (desamino[$Tyr^{10}$,$Phe^{12}\psi(CH_2NH)$-$Gly^{13}$]OGP(10–14)), desamino Tyr-Gly-Phe-NH-$CH_2$-$CH_2$-Gly (SEQ ID NO: 50) (desamino[$Tyr^{10}$,$Gly^{13}\psi(CH_2)_2Gly^{14}$]OGP(10–14)), desamino Tyr-Gly-Phe-NH-$CH_2$-$CH_2$-$CH_2$-$CH_2$-C(O)-OH (SEQ ID NO: 51) (desamino[$Tyr^{10}$,$Gly^{13}\psi(CH_2)_2(Gly^{14})$] OGP(10–14)), Tyr-Gly-NH-CH($CH_2C_6H_4$-(C(O)-$C_6H_5$))-C (O)-Gly-Gly (SEQ ID NO: 56) ([$Bpa^{12}$]OGP(10–14)), Tyr (m-I)-Gly-NH-CH($CH_2C_6H_4(C(O)C_6H_5)$)C(O)-Gly-Gly (SEQ ID NO: 57) ([Tyr(m-I),Bpa$^{12}$]OGP(10–14)) and Nα-biotinylcaproyl-[Bpa$^{12}$]OGP(10–14) (SEQ ID NO: 58).

3. Pseudopeptidic osteogenic growth factor antagonists being Leu-N(CH$_3$)-CH-CH$_2$C$_6$H$_4$(OH))-C(O)-Gly-Phe-Gly-Gly (SEQ ID NO 59) ([N(CH$_3$)Tyr$^{10}$])OGP(9–14)) and Tyr-Gly-Phe-Gly-Asp (SEQ ID NO 29) ([Asp$^{14}$]OGP (10–14)).

4. Pharmaceutical composition comprising as active ingredient at least one pseudopeptide of claim 1, optionally with a pharmaceutically acceptable carrier.

5. Pharmaceutical composition according to claim 4 wherein said pseudopeptide is desamino[Tyr$^{10}$]OGP(10–14) (SEQ ID NO 4).

6. A pseudopeptide according to claim 1 or claim 2 for use in the preparation of a pharmaceutical composition for stimulating the formation of osteoblastic or fibroblastic cells, enhancing bone formation in osteopenic pathological conditions, repairing fractures, healing wounds, grafting of intraosseous implants, reversing bone loss in osteoporosis and other conditions requiring enhanced bone cells formation.

7. A pseudopeptide according to claim 2, for use in the preparation of a pharmaceutical composition for stimulating the formation of osteoblastic or fibroblastic cells, enhancing bone formation in osteopenic pathological conditions, repairing fractures, healing wounds, grafting intraosseous implants, reversing bone loss in osteoporosis and other conditions requiring enhanced bone cell formation.

\* \* \* \* \*

SEQUENCE LISTING

<160> NUMBER OF SEQ ID NOS: 61

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Ala Leu Lys Arg Gln Gly Arg Thr Leu Tyr Gly Phe Gly Gly
 1               5                  10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Gly Gly
 1

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Gly Gly
 1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 4

Tyr Gly Phe Gly Gly
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Gly Gly
 1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 6
```

Tyr Gly Phe Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 7

Tyr Gly Phe Gly Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 8

Tyr Gly Phe Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 9

Tyr Gly Phe Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 10

Tyr Gly Phe Gly Gly
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<221> NAME/KEY: MOD_RES
<222> LOCATION: (1)
<223> OTHER INFORMATION: desamino-Tyr

<400> SEQUENCE: 11

Tyr Gly Phe Gly
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 12

Tyr Gly Phe Gly
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 13

Tyr Gly Phe Gly
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Phe Gly Gly
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Ala Gly
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Gly Phe Gly Ala
 1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Gly Phe Gly Gly
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ala Phe Gly Gly
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Ala

<400> SEQUENCE: 19

Ala Gly Phe Gly Gly
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 20

Tyr Ala Phe Gly Gly
 1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
```

```
<400> SEQUENCE: 21

Tyr Gly Ala Gly Gly
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 22

Tyr Gly Phe Ala Gly
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr

<400> SEQUENCE: 23

Tyr Gly Phe Gly Ala
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Gly Phe Gly Gly
 1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Phe

<400> SEQUENCE: 25

Phe Gly Phe Gly Gly
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<221> NAME/KEY: MOD_RES
<222> LOCATION: (1)..(2)
<223> OTHER INFORMATION: desamino-Phe

<400> SEQUENCE: 26

Phe Phe Gly Phe Gly Gly
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: desamino-Gly

<400> SEQUENCE: 27

Tyr Gly Phe Gly Gly
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Beta-Ala

<400> SEQUENCE: 28

Tyr Ala Phe Gly Gly
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gly Phe Gly Asp
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Pro Phe Gly Gly
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<221> NAME/KEY: MOD_RES
<222> LOCATION: (1)
<223> OTHER INFORMATION: desamino-Tyr
<221> NAME/KEY: MOD_RES
<222> LOCATION: (2)
<223> OTHER INFORMATION: Sar

<400> SEQUENCE: 31

Tyr Xaa Phe Gly Gly
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (3)
<223> OTHER INFORMATION: N(Me)Phe

<400> SEQUENCE: 32

Tyr Gly Phe Gly Gly
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (4)
<223> OTHER INFORMATION: Sar

<400> SEQUENCE: 33

Tyr Gly Phe Xaa Gly
 1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (5)
<223> OTHER INFORMATION: Sar

<400> SEQUENCE: 34

Tyr Gly Phe Gly Xaa
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 35

Tyr Gly Phe Gly Gly
1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Gly Phe Gly
1

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Phe Gly Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Gly Phe Gly Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Beta-Ala

<400> SEQUENCE: 39

Ala Tyr Gly Phe Gly Gly
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: gama-Abu

<400> SEQUENCE: 40

```
Xaa Tyr Gly Phe Gly Gly
  1               5
```

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: delta-Ala

<400> SEQUENCE: 41

```
Ala Tyr Gly Phe Gly Gly
  1               5
```

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Tyr Gly Phe Gly Asp
  1               5
```

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gly Tyr Gly Phe Gly Asp
  1               5
```

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: beta-Ala

<400> SEQUENCE: 44

```
Ala Tyr Gly Phe Gly Asp
  1               5
```

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: gama-Abu

<400> SEQUENCE: 45

Xaa Tyr Gly Phe Gly Asp
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: delta-Ala

<400> SEQUENCE: 46

Ala Tyr Gly Phe Gly Asp
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)..(2)
<223> OTHER INFORMATION: desamino-Tyr-psi-(CH2NH)-Gly

<400> SEQUENCE: 47

Tyr Gly Phe Gly Gly
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (2)..(3)
<223> OTHER INFORMATION: Gly-psi-(CH2NH)-Phe

<400> SEQUENCE: 48

Tyr Gly Phe Gly Gly
 1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (3)..(4)
<223> OTHER INFORMATION: Phe-psi-(CH2NH)-Gly

<400> SEQUENCE: 49

Tyr Gly Phe Gly Gly
 1               5

```
<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (4)..(5)
<223> OTHER INFORMATION: Gly-psi-(CH2NH)-Gly

<400> SEQUENCE: 50

Tyr Gly Phe Gly Gly
  1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: desamino-Tyr
<221> NAME/KEY: MOD_RES
<222> LOCATION: (4)..(5)
<223> OTHER INFORMATION: Gly-psi-(CH2)2-Gly

<400> SEQUENCE: 51

Tyr Gly Phe Gly Gly
  1               5

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)..(4)
<223> OTHER INFORMATION: Gly-psi-(CH2)2-Gly

<400> SEQUENCE: 52

Gly Phe Gly Gly
  1

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: N(Me)-Tyr

<400> SEQUENCE: 53

Leu Tyr Gly Phe Gly Gly
  1               5

<210> SEQ ID NO 54
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<221> NAME/KEY: MOD_RES
<222> LOCATION: (10)
<223> OTHER INFORMATION: N(Me)-Tyr

<400> SEQUENCE: 54

Ala Leu Lys Arg Gln Gly Arg Thr Leu Tyr Gly Phe Gly Gly
 1               5                  10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (9)..(10)
<223> OTHER INFORMATION: Leu-psi-(CH2NH)-Tyr

<400> SEQUENCE: 55

Ala Leu Lys Arg Gln Gly Arg Thr Leu Tyr Gly Phe Gly Gly
 1               5                  10

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Bpa

<400> SEQUENCE: 56

Tyr Gly Xaa Gly Gly
 1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Tyr(m-I)
<221> NAME/KEY: MOD_RES
<222> LOCATION: (3)
<223> OTHER INFORMATION: Bpa

<400> SEQUENCE: 57

Xaa Gly Xaa Gly Gly
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: N-alpha-biotinylcaproyl-Bpa

<400> SEQUENCE: 58
```

```
Tyr Gly Xaa Gly Gly
  1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Tyr Gly Phe Gly Gly
  1               5

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Phe Gly Tyr Leu Thr Arg Gly Gln Arg Lys Leu Ala
  1               5                  10

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Gly Phe Gly Gly
  1               5
```